US 6,605,082 B2
(12) United States Patent  
Hareyama et al.
(10) Patent No.: US 6,605,082 B2
(45) Date of Patent: Aug. 12, 2003

(54) THERMAL TREATMENT APPARATUS

(75) Inventors: Norihiko Hareyama, Tokyo (JP); Toru Nagase, Tokyo (JP); Makoto Inaba, Tokyo (JP); Takefumi Uesugi, Tokyo (JP); Satoshi Mizukawa, Tokyo (JP); Shin Maki, Kanagawa (JP); Shigeki Ariura, Kanagawa (JP)

(73) Assignees: Olympus Optical Co., Ltd., Tokyo (JP); Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/895,408

(22) Filed: Jul. 2, 2001

(65) Prior Publication Data
US 2002/0022869 A1 Feb. 21, 2002

(30) Foreign Application Priority Data
Jul. 3, 2002 (JP) ......................... 2000-201645

(51) Int. Cl.[7] .............................. A61B 18/22
(52) U.S. Cl. ..................... 606/11; 606/14; 606/15; 606/19
(58) Field of Search .................. 606/10–18; 607/88–89

(56) References Cited

U.S. PATENT DOCUMENTS

| | | |
|---|---|---|
| 4,932,956 A | 6/1990 | Reddy et al. |
| 5,207,672 A | 5/1993 | Roth et al. |
| 5,292,320 A | 3/1994 | Brown et al. |
| 5,496,308 A | 3/1996 | Brown et al. |
| 5,788,688 A * | 8/1998 | Bauer et al. ............... 606/1 |
| 6,149,643 A * | 11/2000 | Herekar et al. ............ 606/10 |
| 6,159,205 A * | 12/2000 | Herekar et al. ............ 606/10 |
| 6,203,540 B1 * | 3/2001 | Weber ..................... 606/11 |
| 6,322,555 B1 * | 11/2001 | LaHaye ................... 128/898 |

FOREIGN PATENT DOCUMENTS

| | | |
|---|---|---|
| EP | 0 673 627 A1 | 3/1995 |
| EP | 0 947 221 A2 | 10/1999 |
| EP | 0 960 601 A2 | 12/1999 |
| JP | 8-164135 A | 6/1996 |
| JP | 8-318001 A | 12/1996 |
| JP | 10-192427 A | 7/1998 |
| WO | WO 92/04934 A1 | 4/1992 |
| WO | WO 93/04727 A1 | 3/1993 |

* cited by examiner

Primary Examiner—Roy D. Gibson
Assistant Examiner—Henry M. Johnson, III
(74) Attorney, Agent, or Firm—Burns, Doane, Swecker & Mathis, LLP

(57) ABSTRACT

The invention relates to a thermal treatment apparatus capable of irradiating targeted lesions with energy to obtain good treatment results.

The invention displays the diagnostic images 2201 of the lesion overlaid upon the laser irradiation areas a, b, c, and d and is capable of setting up the laser emission angle, output and time using the graphical user interface displayed on the touch panel.

36 Claims, 24 Drawing Sheets

THERMAL TREATMENT APPARATUS

BACKGROUND OF THE INVENTION

1. Field of the Invention

The invention relates to an apparatus for thermal treatment by means of irradiating lesions of body tissues with various forms of energies such as laser beams, microwaves, radio frequency, and ultrasonic waves.

2. Description of the Prior Arts

Various thermal treatment apparatuses have been known for treating lesions to reduce or eliminate them by means of heating, alteration, sphacelation, coagulation, cauterization or evaporation of lesions by irradiating them with energies, such as laser beams, microwaves, radio frequency, and ultrasonic waves, with a long main unit inserted into a human body either via a body cavity or an opening produced by a small incision.

A technique has also been known for treating a lesion hidden deep in an organ, such as prostate, by applying heat through energy irradiation. For example, the Published Japanese Translation of PCT Patent Application H6-510450 disclosed a technology for coagulating and reducing a tumor or a portion of the prostate tissue by means of laser beam irradiation. The feature of said technology is to heat mainly the inside of the prostate while avoiding the heating of the surface of the urethra that contacts a balloon by feeding a coolant into the balloon.

In the abovementioned thermal treatment apparatuses, it is mandatory to conduct image diagnoses of the tissues that include the lesions, which are the targets of thermal treatments, or their surrounding tissues, to know the shapes of the tissues including the lesions, their positional relations with the surrounding tissues, shapes of the lesions, and the graveness of the diseases. For such a diagnostic purpose, it has been customary to use apparatuses designed specifically for image diagnosis, i.e., separate units not included in said thermal treatment apparatuses.

Based on the result of such an image diagnostic apparatus and the experience of the operator, individual treatment conditions including the intensity (output) of the energy such as laser beam, microwave, radio frequency and ultrasonic wave, irradiation period, irradiation direction, irradiation position, number of irradiation applications, coolant temperature if a coolant is used, and coolant flow rate if a coolant circulation is used, are separately established.

In the thermal treatment apparatuses of the prior arts, it is necessary for the operator to understand the image diagnosis information and enter the treatment condition into the thermal treatment apparatuses. Therefore, the input work has been cumbersome, has taken a long time for the operator in preparation for a thermal treatment, and has generally caused a heavy burden on the operator.

SUMMARY OF THE INVENTION

The present invention is made considering the status of the prior arts and its object is to reduce the burden on the operator as the operator prepares for a thermal treatment by providing a thermal treatment apparatus for which a treatment condition can be set up according to the shape of the lesion of the patient.

The stated object can be achieved by a thermal treatment apparatus that conducts thermal treatments by means of irradiating living bodies with energy comprising: an energy supply means for supplying energy for treatment; an energy irradiating means for irradiating the supplied energy to a living body; a treatment planning means for setting up a treatment area to be irradiated by the energy as treatment area information; a setup means for setting up a treatment condition to be irradiated by the energy; an input means for inputting image information for diagnosis; an information overlaying means for overlaying the treatment area information already set up and the image information already inputted; and an information manipulating means for manipulating at least either one of the treatment area information or the image information.

The stated object can also be achieved by a thermal treatment apparatus that conducts thermal treatments by means of irradiating living bodies with energy comprising: an energy supply means for supplying energy for treatment; an energy irradiating means for irradiating the supplied energy to a living body; a treatment planning means for setting up at least two treatment areas to be irradiated by the energy; a selecting means for selecting a treatment area among the treatment areas already set up; a setup means for setting up a treatment condition to be irradiated by the energy.

DETAILED DESCRIPTION OF THE INVENTION

Preferred embodiments of the present invention will be described below in detail with reference to the accompanying drawings.

Figure 1:
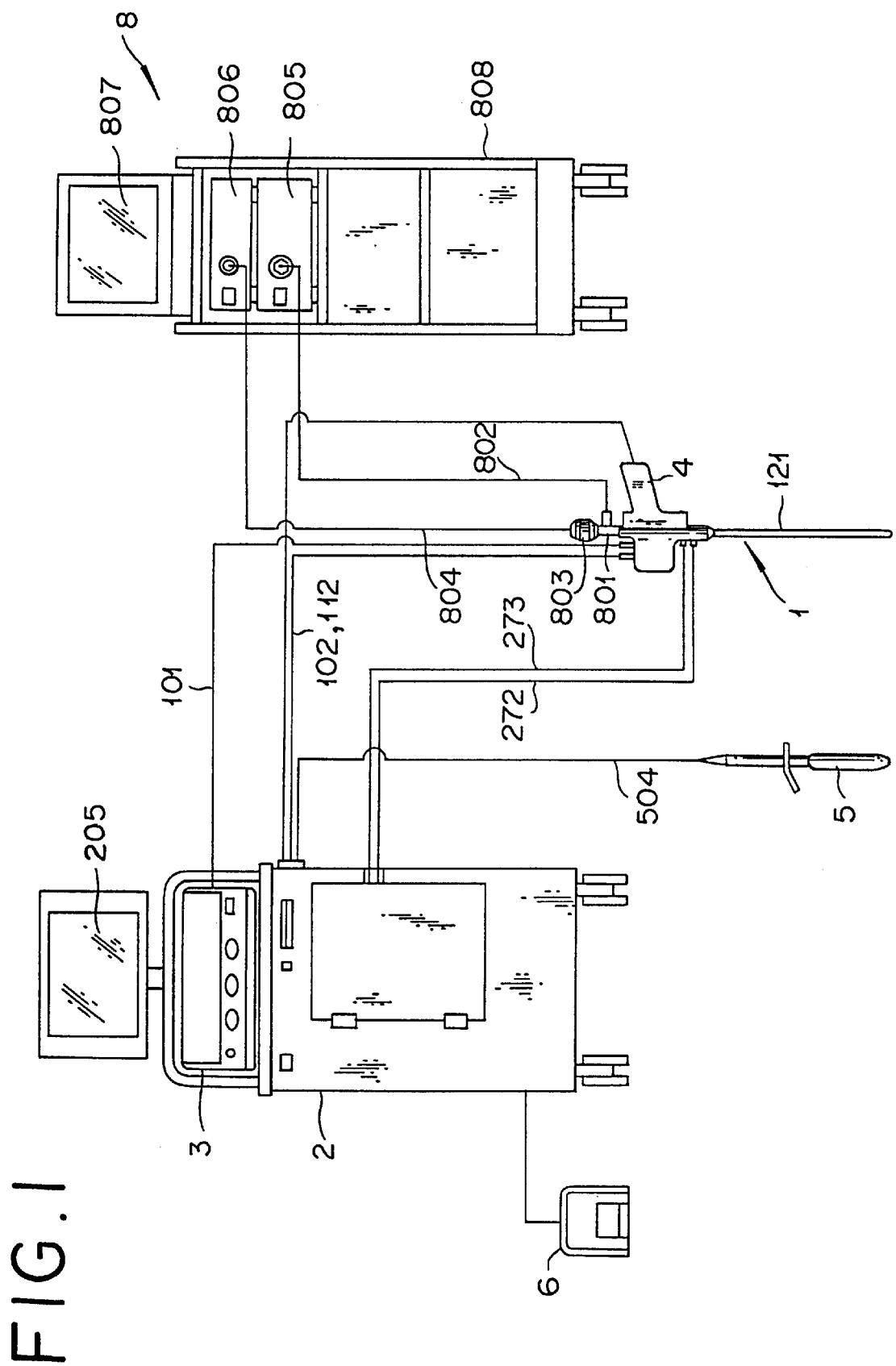
FIG. 1 is a block diagram showing the overall constitution of a thermal treatment apparatus according to the embodiment in this invention.

FIG. 1 is a schematic drawing for describing the entire constitution of the thermal treatment apparatus according to the present invention.

The thermal treatment apparatus of this embodiment includes, as shown in FIG. 1, a laser beam irradiation unit 1, a control main body 2, a laser beam generator 3, a drive unit 4, a rectum probe 5, a footswitch 6, and an observation unit 8. The laser beam irradiation unit 1, the laser beam generator 3, the drive unit 4, the rectum probe 5, and the footswitch 6 are connected to the control main body 2. The footswitch 6 sends a signal to a control main body 2 prompting laser beam irradiation when the operator steps on it.

The laser beam irradiation unit 1 is intended for thermal treatment by irradiating tissues with laser beams and used for the treatment of BPH (Benign Prostatic Hyperplasia), various tumors such as cancer, etc. (to be described in detail later).

The control main body 2 controls the entire operation of the thermal treatment apparatus using the detection signals from various sensors and micro switches built into the laser beam irradiation unit 1, the drive unit 4, and the rectum probe 5, is used for preparing treatment plans using a touch panel (touch screen) display 205, issues various instructions based on the treatment plans and collects data during treatments as mentioned later.

The observation unit 8 is equipped with a light source unit 805 that supplies illumination light for endoscope observation, a TV camera unit 806 for capturing images observed by an endoscope, an image receiver 807 for displaying images captured by the television camera unit 806, and a movable cart 808 carrying all of these units. A light source 805 is connected to a light guide 802. A TV camera 806 is connected to a camera head 803 via a camera signal lead 804. Thus, it is possible to perform thermal treatments observing through an endoscope 801.

Figure 2:
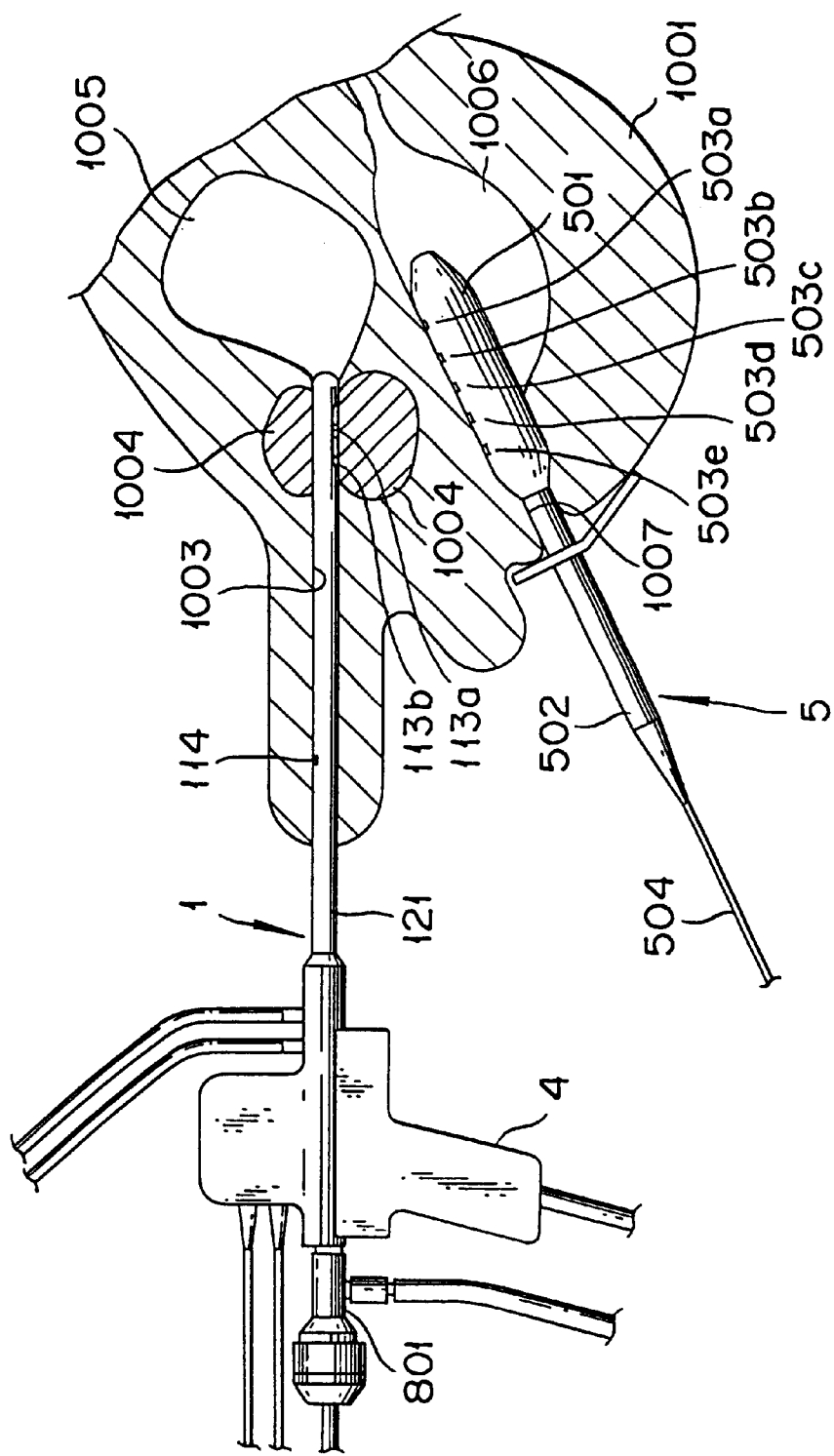
FIG. 2 is across section showing an example of using said thermal treatment apparatus used for prostate treatment.

As shown in FIG. 2 (also refer to FIG. 3), a long insertion part 121 of the laser beam irradiation unit 1 is inserted into a living body and the laser beam irradiation unit 1 irradiates laser beams to a tissue 1001 from a laser emission unit 122 (refer to FIG. 3) provided in a housing 124 of the insertion part 121.

A cap 126 seals the distal end of the housing 124. An optical fiber 101 is placed inside the insertion part 121 for guiding the laser beam. A lens can be provided at the distal end of the optical fiber 101. The lens is an optical device for converting laser beams into collimating beams. The optical fiber 101 transmits the laser beams generated by the laser generator 3.

The optical fiber that guides the laser beam and the endoscope are both guided to the vicinity of the distal end of the insertion part through a lumen (not shown) of the insertion part 121. Also, another lumen for cooling water (not shown) is provided inside the insertion part 121, and this lumen for cooling water is connected to a water supply tube 272 and a water drain tube 273 (refer to FIG. 1). Circulation of the cooling water improves the cooling efficiency. The lumen for cooling water should preferably be equipped with a check valve in order to prevent the water from flowing in the opposite direction to the proximate end.

The insertion part 121 of the laser beam irradiation unit 1 is inserted into the urethra 1003 and the vicinity of the distal end of the insert part 121 where the laser emission unit is installed is made to contact with the surface layer of the prostate 1004. The item 1005 in the drawing represents the bladder. Urethra temperature sensors 113a and 113b are provided to detect the temperatures of the urethra wall inside the insertion part 121 in the vicinity of its distal end. The signals from the urethra temperature sensors 113a and 113b are led to the control main body 2 (refer to FIG. 4) through sensor lead wires 102.

Meanwhile, the endoscope 801 is connected to the proximal part of the laser beam irradiation unit 1 in order to make it possible to observe the inside of the human body while conducting a thermal treatment.

A rectum probe 5 has an insertion part 501, which is inserted into the rectum 1006 through the anus 1007 as shown in FIG. 2, and a grip 502, which is held by the operator. The insertion part 501 of the rectum probe 5 is provided with multiple rectum temperature sensors 503a through 503e for detecting the temperatures of the rectum wall, and the detected values are transmitted through sensor signal lead wire 504. The rectum temperature sensors 503a through 503e are not implanted in tissues but rather placed deep inside the prostate 1004 seen from the urethra 1003.

Therefore, this thermal treatment apparatus is capable of conducting a thermal treatment using the results of urethra wall temperature and rectum wall temperature detections. This way it is possible to prevent the normal tissues of the urethra and the rectum existing in the vicinity of the prostate being unnecessarily heated.

The temperature sensors that can be used as the urethra temperature sensors 113a and 113b are thermistors, thermocouples, and platinum temperature measuring resistors, but the thermocouple or the thermistor are the most preferable because the thermocouple is smaller so that its effect on laser beam irradiation is minimum and the thermistor is inexpensive. As to the temperature sensors that can be used as the rectum temperature sensors 503a through 503e are also thermistors, thermocouples, and platinum temperature measuring resistors, but the thermistor is the most preferable because it is inexpensive.

Figure 3:
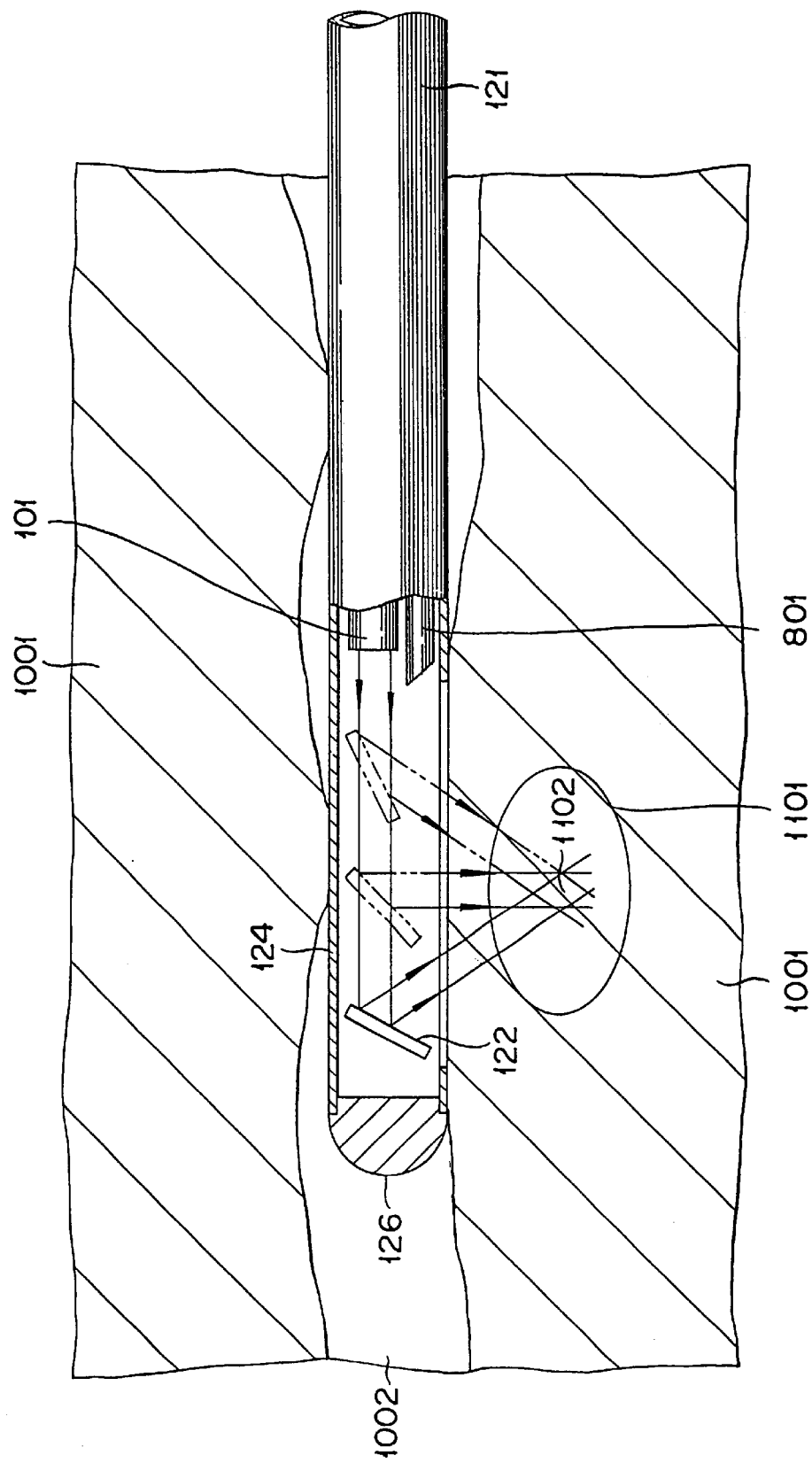
FIG. 3 is a cross section for describing an example of using a laser beam irradiation apparatus.

FIG. 3 is a cross section for describing an example of using the laser beam irradiation unit 1 in the human body.

The distal end of the insertion part 121 is inserted into a body cavity 1002 and the housing 124 that contains the laser emission part 122 is made to contact with the surface layer in the vicinity of a target location 1101, which is the lesion, in other words, the area to be heated. In this case, it is preferable to confirm directly the location of the housing 124 by means of the endoscope 801. The location of a target point 1102 in the longitudinal direction of the insertion part 121 is adjusted by moving the entire laser beam irradiation unit 1 in the longitudinal direction of the insertion part 121. The position of the target point 1102 in the circumferential direction of the insertion part 121 is adjusted by rotating the entire laser beam irradiation apparatus 1.

In the irradiation of the laser beam, the laser emission part 122 preferably makes a reciprocating motion in the axial direction at the frequency of 0.1 through 8 Hz, preferably 3 through 6 Hz while changing the irradiation angle. Although the path of the laser beam thus emitted changes continuously, all the resultant beams cross each other at the target point 1102.

As a result, the target point 1102 and its vicinity in side body tissues 1001 get heated by the irradiated beams and reach a desired temperature. Thus, it is possible to raise only the temperature at the desired target area 1101 without raising the temperature at the surface layer part. The laser beam irradiation part 122 is a mirror that reflects the laser beam as shown in FIG. 3.

The laser beam used for irradiating the tissue 1001 can be a divergent beam, a collimating beam, or a convergent beam. In order to make a laser beam a convergent beam, an optical system that makes the laser beam the convergent beam is provided in the passage of the beam. Any laser beam can be used for the purpose of the invention as long as it is transmissible to living tissue. However, the wavelengths of the laser beams are preferably 750 nm through 1300 nm or 1600 nm through 1800 nm as they have particularly good depth-reaching capabilities. Therefore, the laser beam generating device 3 for generating laser beams in said wavelength ranges should preferably be a generator that generates either gas laser beams such as the He—Ne laser beam, solid laser beams such as the Nd-YAG laser beam, or semiconductor laser beams such as the GaAlAs laser beam.

The diameter of the insertion part of the laser beam irradiation unit 1, i.e., the outer diameter of the insertion part 121 can be arbitrary as long as it can be inserted into the body cavity 1002. However, the output diameter of the insertion unit 121 is preferably 2 to 20 mm, or more preferably 3 to 8 mm.

Figure 4:
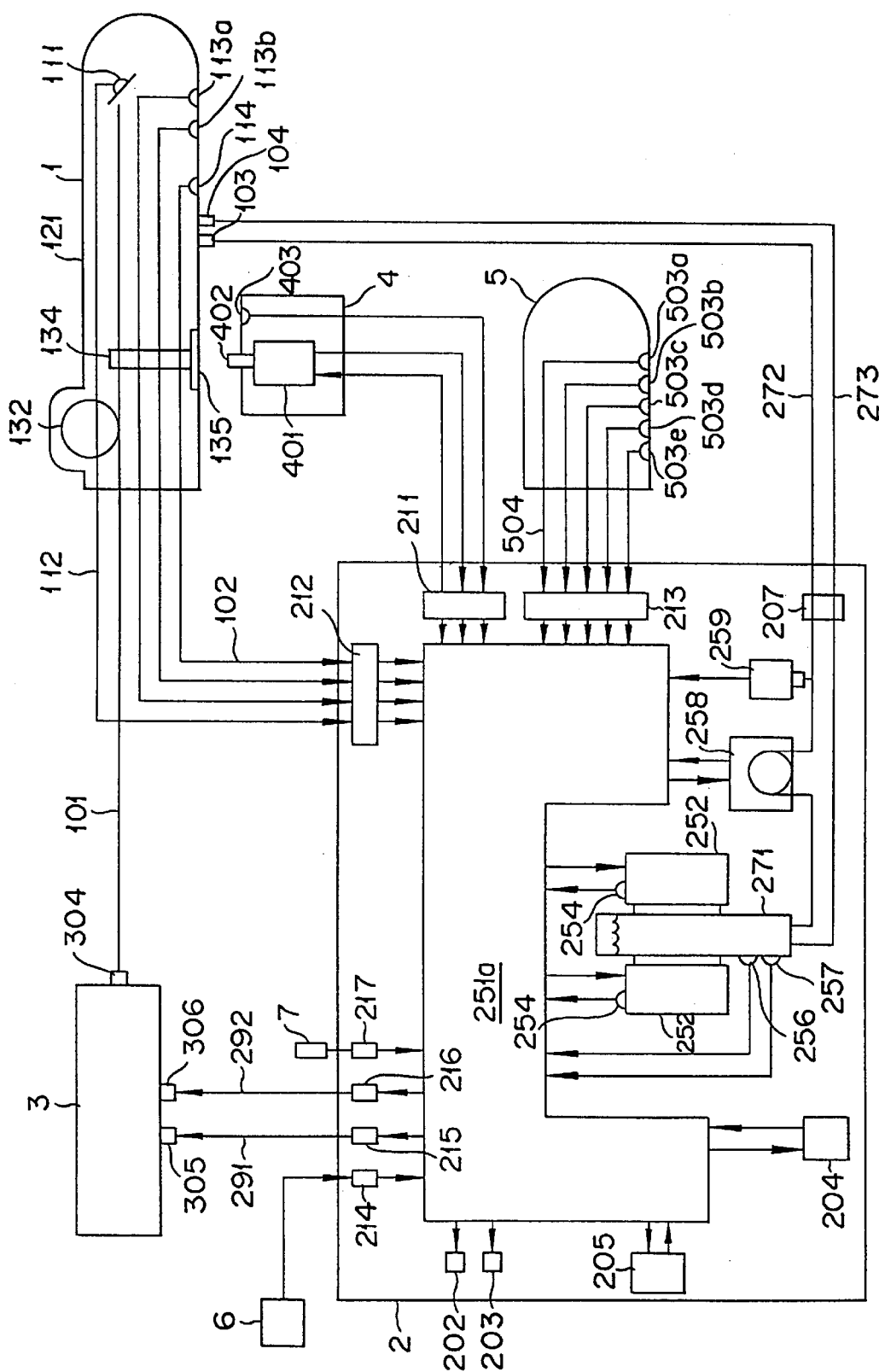
FIG. 4 is a block diagram of control system primarily showing the control main body of the thermal treatment apparatus.
Figure 5:
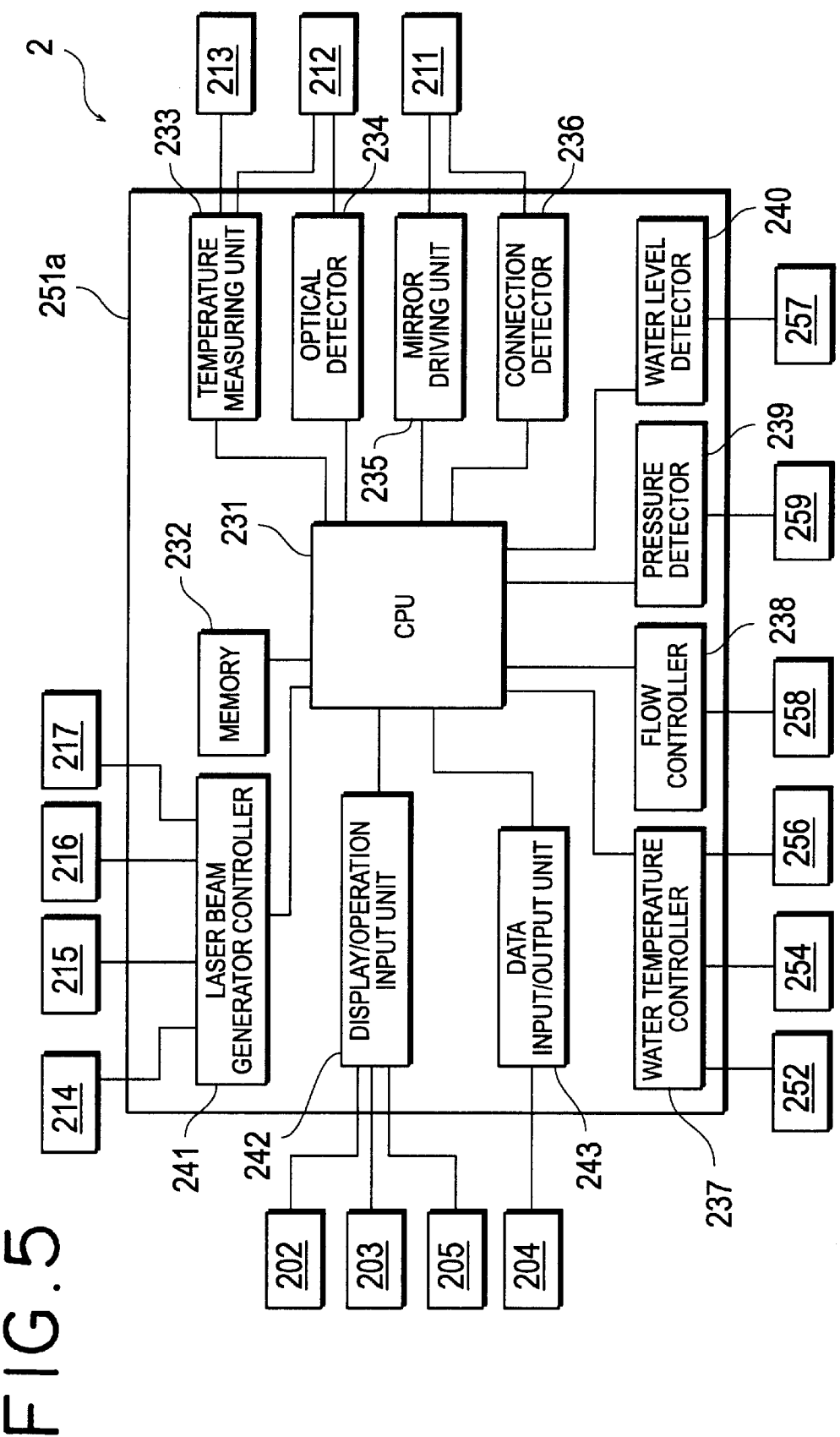
FIG. 5 is a diagram for describing the detail of the control main body shown in FIG. 4.

The control main body 2 has a controller 251a as shown in FIG. 4 and FIG. 5. As shown in FIG. 5, the controller 251a is equipped with peripheral controllers such as a temperature measurement unit 233, a light detector 234, a mirror drive unit 235, a connection detector 236, a water temperature controller 237, a flow controller 238, a pressure detector 239, a water level detector 240, a laser generator controller 241, a display/operation input unit 242, and a data input/output unit 243, a CPU 231 for controlling such peripheral controllers integrally, input/output control for preparing treatment plans, preparing data, and screen display control, and a memory 232 for storing specified programs and data.

The temperature measuring unit 233 receives detection signals from a temperature sensor 111 that detects the temperature of the laser emission part and from urethra temperature sensors 113a and 113b via a urethra sensor connector 212, as well as detection signals from rectum temperature sensors 503a through 503e via a rectum sensor connector 213. The light detector 234 receives a detection signal from an optical sensor 114 via a urethra sensor connector 212. The light sensor 114 is installed in the laser beam irradiation unit 1 and detects optically if the insertion part 121 of the laser beam irradiation unit 1 is not abutting the object of irradiation by the laser beam. This makes it possible, for example, to prevent the laser beam from being emitted under the condition that the insertion part 121 is not inserted in the human body. The item 112 in the drawing is the sensor lead wire for transmitting the signal from the temperature sensor 111 for detecting the temperature of the laser emission part to the control main body 2.

The mirror drive unit 235 is connected to a motor 401 of the drive unit 4 via a connector 211 and exchanges signals. The drive signal is sent by the mirror drive unit to the motor 401. The motor 401 has a detection means (not shown) for detecting rotating speeds, rotating angular positions, and rotating loads and the signals from these detection means are fed back to the mirror drive unit.

The connection detector 236 receives detection signals from a micro switch 403 that detects whether the drive unit 4 is connected to the laser beam irradiation unit via the drive unit connector 211. Said connection of the drive unit 4 is made by connecting a drive force transmitting part 402 with a driving power receiving part 135, which is mounted on the insertion part 121 via a support part 134. The base part of the insertion part 121 is provided with a cushioning unit 132, which absorbs the movement of the optical fiber by storing the optical fiber forming a loop.

The water temperature controller 237 receives detection signals from a water temperature sensor 256, and the water temperature controller 237 issues a signal for cooling to the cooling element 252. The water temperature controller 237 also stops the operation of the cooling element 252, if the excessively high [sic] temperature is detected by a thermostat 254 installed on the cooling element 252. Thus, the temperature of the circulating cooling water can be maintained at a preferred temperature. The water level detector 240 receives detection signals from a water level sensor 257 so that it is possible to judge if the necessary amount of the cooling water is maintained.

The flow controller 238 is connected to a pump 258 to exchange signals. The flow controller 238 issues drive signals to the pump 258, and the pump 258 feeds back detection signals concerning the flow rate and others. This makes it possible to control the flow rate. Roller pumps, diaphragm pumps, magnet pumps, etc., can be uses as the pump 258.

The pressure detector 239 receives detection signals from a pressure sensor 259 that detects the water pressure in the water supply tuber 272. Monitoring the detection results of the pressure sensor 259 makes it possible to avoid situations in which the cooling water reaches excessively high pressures. The item 207 is a tube panel where the water supply tube 272 and the water drain tube 273 are connected. The item 271 is a bag that contains the cooling water.

The laser beam generator controller 241 receives signals from the footswitch 6 via a footswitch signal input connector 214. The laser beam generator controller 241 issues signals for outputting laser beams to the laser beam generator 3 via a footswitch signal cable 291 connected to a footswitch signal output connector 215. When it receives signals from an interlock switch 7 via an interlock switch signal input connector 217, the laser beam generator controller 241 issues signals for stopping the output of laser beams to the laser beam generator 3 via an interlock switch signal cable 292 connected to an interlock switch signal output connector 216. The interlock switch 7 issues signals to stop the operation of the laser beam generator 3 interlocking with, for example, the signal that the door of the laser management area is opened. The item 305 is a footswitch signal input connector of the laser beam generator 3, and the item 306 is an interlock signal input connector of the laser generator 3. The item 304 is a laser output connector that connects the optical fiber that transmits the laser beam generated by the laser beam generator 3.

The display/operation input unit 242 lights an abnormality warning lamp 202 and outputs a signal for operation to an abnormality warning buzzer 203. The display/operation input unit 242 displays a graphical user interface screen and is connected to a touch panel (touch screen) display 205 that receives various input for operations and instructions for exchanging signals. The display/operation input unit 242 displays certain kinds of information as a graphical user interface screen on the touch panel display 205, while signals corresponding to various settings and instructions by the operator are issued to display/operation input unit 242 via the displayed graphical user interface screen.

The touch panel display 205 is a matrix switch panel consisting of transparent electrodes overlaid on a CRT or a liquid crystal display screen and allows the operator to perform various instructions and data input by simply touching the selected graphical points on the screen. The touch panel display 205 can be replaced with a combination of a CRT or liquid crystal display and a mouse or pen tablet, or any other user interface device.

The data input/output unit 243 is connected to external memory devices (e.g., floppy disk (FD) drive, MO drive, portable hard disk drive, CD-read/write device, etc.) via media interface 204 in order to make it possible to read or write various information concerning the patient such as diagnostic information and thermal treatment history recorded on external memory media (e.g., floppy disk (FD), portable hard disk, MO disk, CD-read/write disk). It is also possible to enter time-shared diagnostic information directly from various image diagnostic devices by connecting it with them, or to input/output information exchanges with memory devices (e.g., external memory devices such as those mentioned above) provided at various image diagnostic devices.

The memory 232 consists of a ROM storing the programs required for controls to be executed by the CPU and treatment plan preparation; a RAM to be used as a work area for various executions of the CPU 231, as a memory device for various setup data, and also as a temporary memory for the patient's diagnostic information and thermal treatment history inputted through the data input/output part 243; and a nonvolatile memory device such as a ROM, EEPROM or flash memory for storing a predetermined user interface screen. The user interface screen, patient's diagnostic information and thermal treatment history can be stored in a separate device such as a HDD.

Next, the operation of a thermal treatment apparatus constituted as described above will be described below.

In an actual treatment using a thermal treatment apparatus, the first step is to prepare a treatment plan. Treatment planning includes determining the location of the laser beam irradiation and the amount of energy to be applied such as the time (duration) of application based on the treatment information specific to the patient such as the location of the lesion and its size, and entering these values in the memory of the control main body 2.

In this embodiment, the touch panel display 205 is used to prepare such a treatment plan easily and securely.

Figure 6:
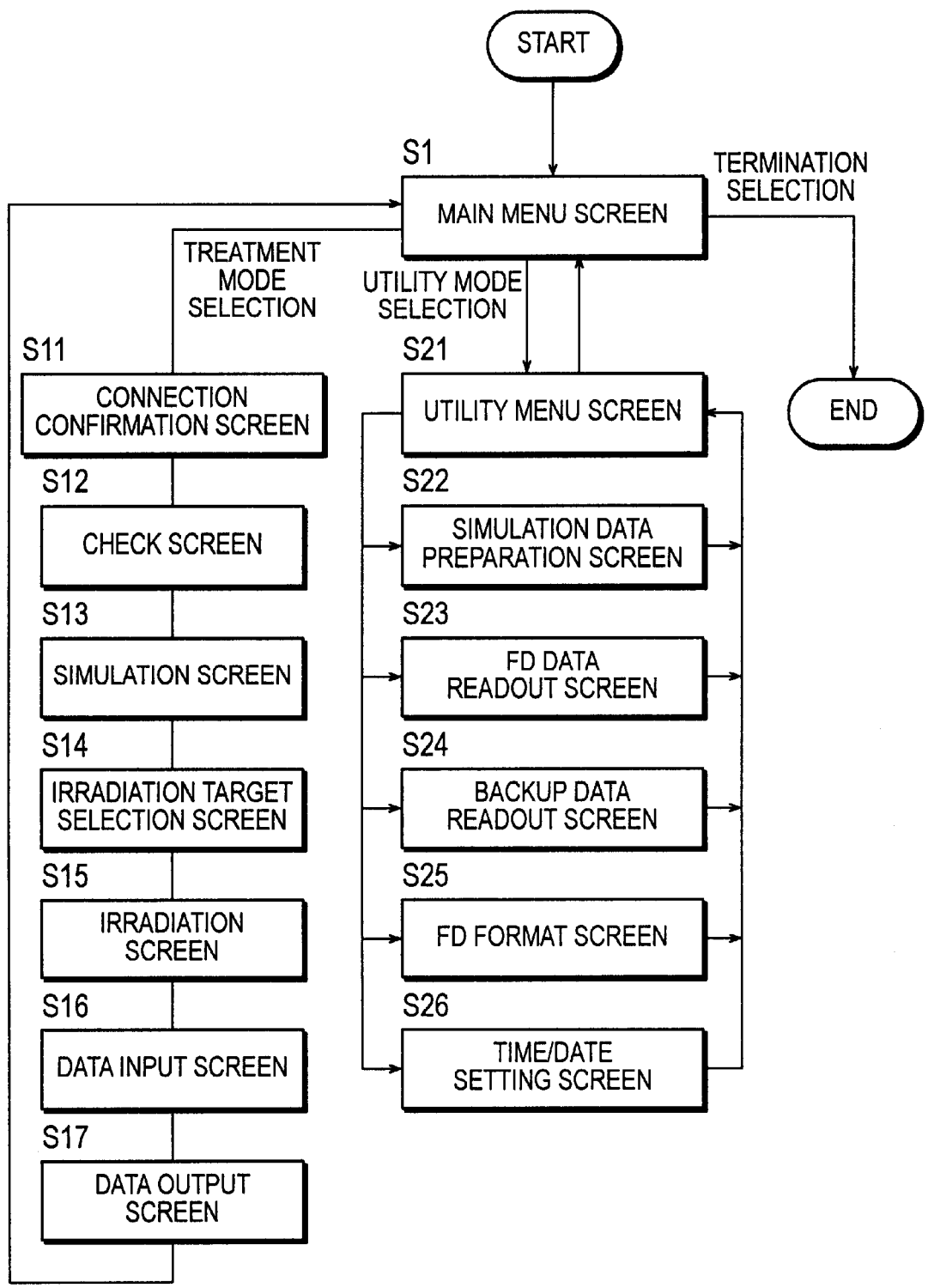
FIG. 6 is a flow chart showing a transition sequence of graphical user interface.

FIG. 6 is a flowchart showing the transition sequence of the graphical interface screen displayed on the touch panel display 205. Each screen is read from the memory 232 according to the instruction of the operator and displayed on the touch panel display 205.

The graphical interface screen displayed on the touch panel display 205 starts with the menu screen display (S1), which allows the operator to make a selection between the treatment mode or the utility mode, or termination of the operation.

When the treatment mode is selected, the connection confirmation screen (S11), the check screen (S12), the simulation screen (S13), and the irradiation target screen (S14) are displayed sequentially in that order to allow the operator to make various settings from each of these screens to complete the treatment plan.

When various settings are completed, the irradiation screen (S15) is displayed to show the instructions for the laser beam irradiation for the actual treatment.

After that, the input screen of the treatment data (S16) and the data output screen (S17) that shows the treatments made up to the date are shown to complete the treatment mode. The details of these treatment mode screens and various settings on these screens will be discussed later.

When the utility mode is selected, a utility menu screen (S21) is displayed first for providing instructions to move to utility screens listed below. Following the instructions displayed on said screen, the operator can move to a simulation data preparation screen (S22) for preparing data required for the simulation of the treatment to be performed on the patient, similar thermal treatment data of other patients obtained from an FD (or other external memory devices), a FD data readout screen (S23) for reading out the patient information, the image data of the lesion, etc., a backup data reading screen (524) for reading backup data, a FD format screen for formatting (initializing) FD (525), or a date/time resetting screen (526).

Among various screens in the utility mode, the simulation data preparation screen (S22) is a screen used prior to entering the treatment mode in preparing the treatment plan when the operator enters the treatment mode for preparing data of the recommended values such as the irradiation condition of the laser beam irradiation energy based on location and size of the lesion of the patient as well as the data of the patients treated in the past or the experiences of the doctors and the operator, etc.

The FD data readout screen (S23) is a screen for reading out the individual data of the patients treated in the past and the data of the patient to be treated, and allows the operator to read the information that specifies a patient such as the patient's name, age, medical record number, and other ID information, as well as the data of the diagnosis results showing the patient's lesion.

The diagnosis of the lesion can be made using optical endoscopes, ultrasonic endoscopes, X-ray contrast radiography, magnetic resonance imaging (MRI), computed tomography (CT) using X-ray or magnetic resonance, positron emission tomography (PET), single photon emission computed tomography (SPECT), etc. From the FD data readout screen (not shown), the data diagnosed by these diagnostic devices are read out and stored in the memory 232 (or HDD). The images of these diagnoses and patient data can also be read out from the simulation screen.

The details of each screen in the treatment mode and the setup operation performed there will be described.

Figure 7:
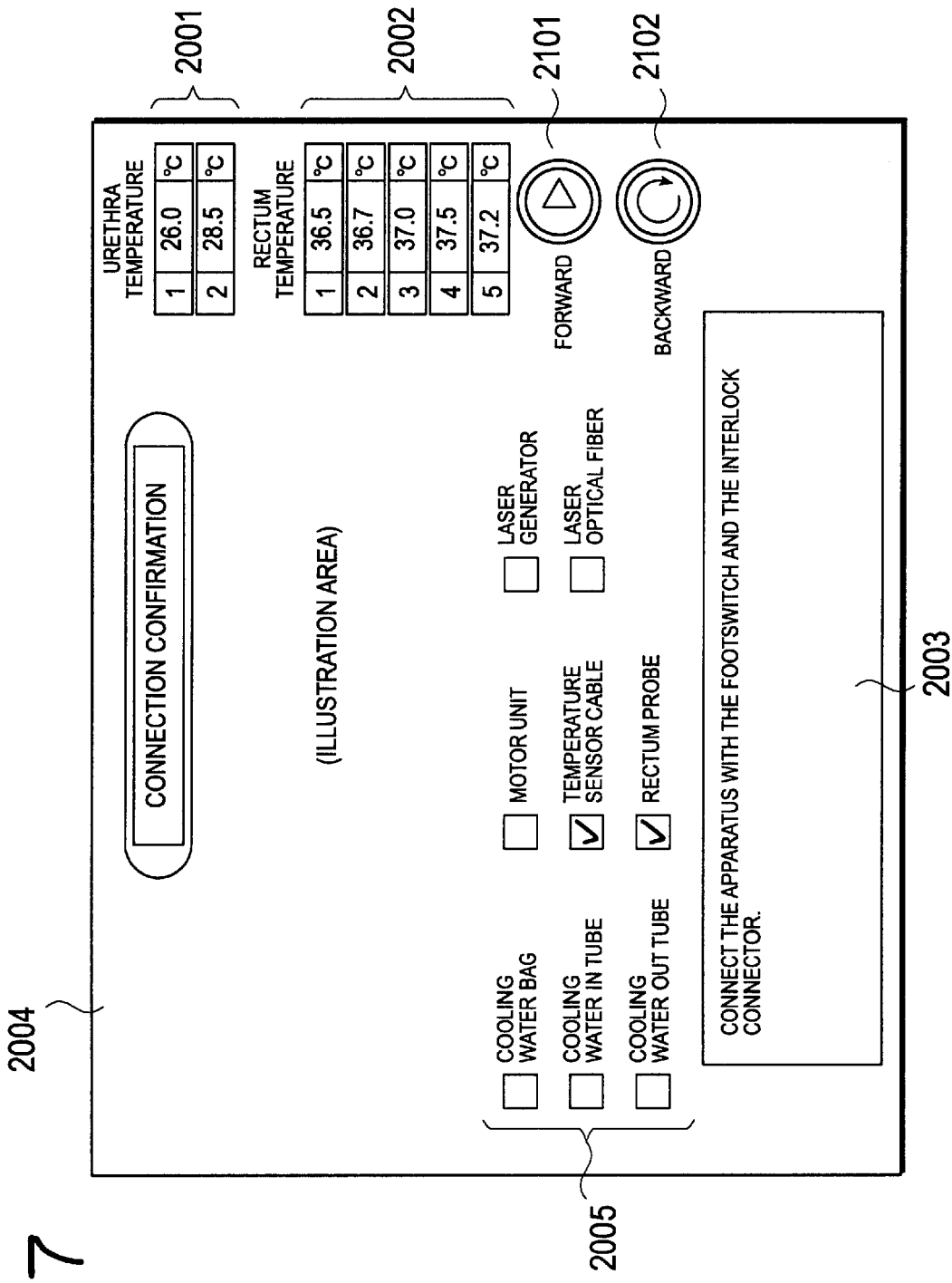
FIG. 7 is a drawing for describing a connection confirmation screen.

For example, the connection screen is an interface screen such as the one shown in FIG. 7, and consists of a urethra temperature display area 2001, a rectum temperature display area 2002, a message area 2003, an illustration area 2004, a list of the names of the devices the operator is checking the connection of and the check boxes 2005, a forward step button 2101 to switch to the next screen, and a backward step button 2102.

This connection screen is provided with the check box 2005 for each device for the operator to check the connection of, and the operator is to place a check mark each time when the operator confirms the connection of the particular device. A message prompting the operator to check connections will be displayed in the message area 2003 as long as there area some check boxes yet to be check marked.

When all the check boxes 2005 are checked and the forward step button 2101 is pressed, the next check screen will be displayed on the touch panel display 205.

Figure 8:
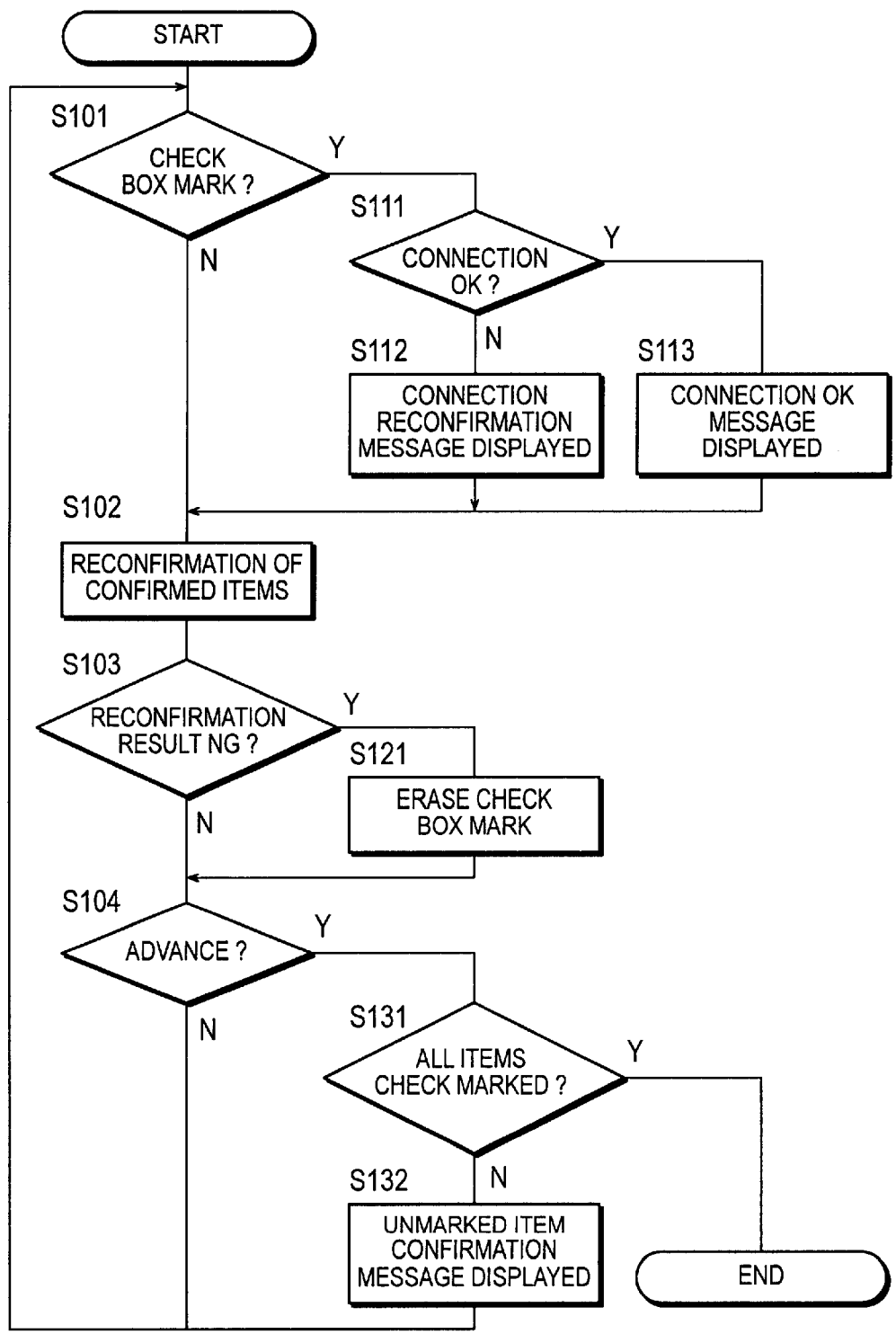
FIG. 8 is a flow chart showing an operation sequence performed on said connection confirmation screen.

FIG. 8 is a flow chart showing an operation sequence performed on said connection confirmation screen.

First, a judgment is made whether one of the check boxes 2005 is check marked (S101). If no check box is check marked at this point, the process advances to the next step S102, and continues the process until a new check box is marked or another button is pressed. On the other hand, if a check mark is placed on a check box, a connection confirmation procedure is executed for said check marked device (S111). This is a process where the control main body 2 automatically confirms the connection which the operator has confirmed visually. If it fails to confirm the connection (S111: N), a message prompting the connection confirmation will be displayed on the message area 2003 (S112), and the process advances to the step S102. On the other hand, if it succeeds in confirming the connection (S111: Y), a message confirming the connection will be displayed (S113), and the process advances to the step S102.

At the step S102, the connection confirmations are repeated on all devices for which connections have been confirmed. If there is any item for which the confirmation is negative (S103: Y), the check mark in the box corresponding to the particular device is removed (S121), and the process proceeds to the next step S104. If there is no negative result (S103: N), the process proceeds straight to the next step S104. The procedures at the steps S102, S103 and S121 are intended for continuing to check the connection status of each device constantly and warn the operator if the connection of a device is broken even after its connection was confirmed and prevents the operator from advancing to the next screen.

Next, at the step S104, a judgment is made whether the forward step button is pressed. If the forward step button has been pressed (S104: Y), it makes a judgment further where all check boxes have been marked (S131), displays a message to confirm the items if there are any unchecked marks (S132), and proceeds to the step S101. Unless all the check boxes are marked, in other words, unless the minimum number of devices is connected, the system does not allow the operator to move to the next screen.

On the other hand, if all items are check marked, the process at this screen is terminated. When the process at the connection screen is terminated, the screen advances to the check screen.

Various messages displayed in the message are 2003 are stored in the memory 232 in advance and the CPU 231 selects and displays them depending on the connection confirmation result (hereinafter the same).

Figure 9:
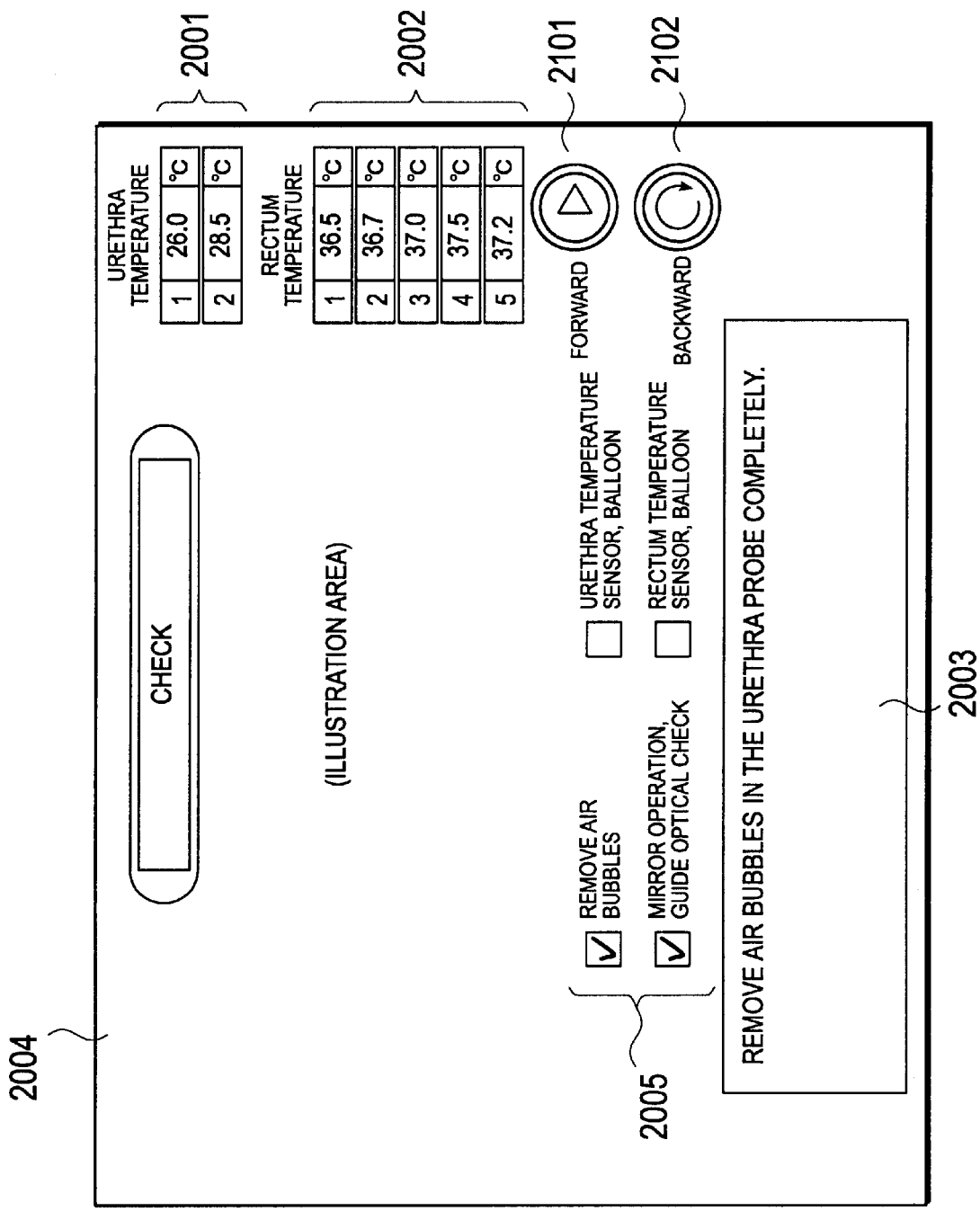
FIG. 9 is a drawing for describing a check screen.

The check screen includes, as shown in FIG. 9 and similar to the connection confirmation screen, the urethra temperature display area 2001, the rectum temperature display area 2002, the message area 2003, the illustration area 2004, the forward step button 2101 to switch to the next screen, and the backward step button 2102, as well as a list of the names of the devices for the operator to check the connection of and the check boxes 2005.

Here again, a device that has been confirmed for operation needs to be check marked in the check box 2005 before it is allowed to proceed to the next step, and a message prompting the operator to confirm the operation will be displayed.

Figure 10:
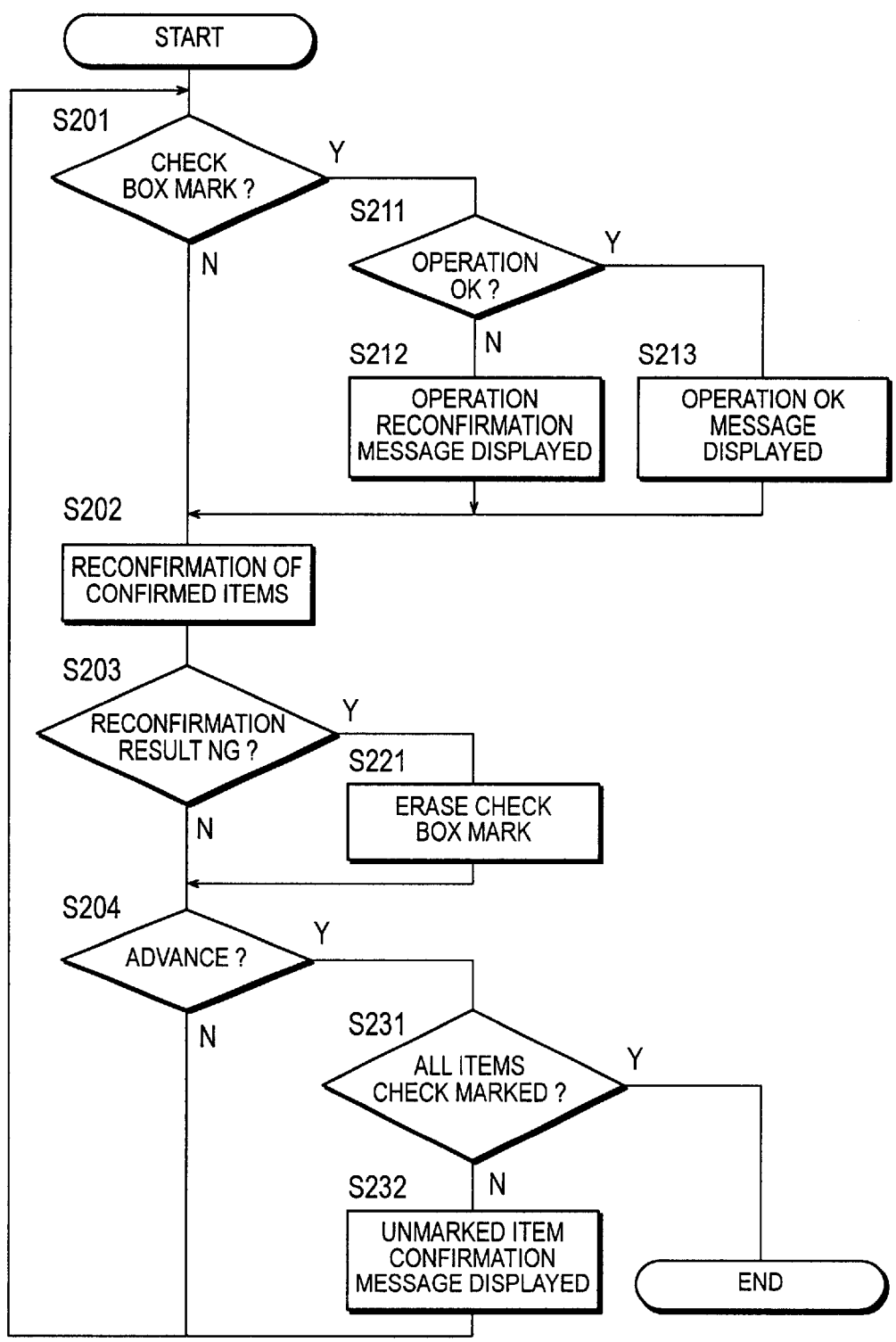
FIG. 10 is a flow chart showing an operation sequence performed on said check screen.

FIG. 10 is a flowchart showing the operation process on this check screen.

First, it is judged whether any check box 2005 is checked (S201). If there is no check box 2005 that has been newly check marked, the process advance to the next step S202, and the process continues until a new check mark is placed or another button is pressed. On the other hand, if a check mark is placed on a check box, an operation confirmation procedure is executed for said check marked device (S211). This is a process where the control main body 2 determines whether any abnormality can be detected by sending electrical signals to the device to cause it to perform its operation, which the operator has confirmed visually. If it fails to confirm the operation (S211: N), a message prompting the operation confirmation will be displayed on the message area 2003 (S212), and the process advances to the step S202. On the other hand, if it succeeds in confirming the operation (S211: Y), a message confirming the connection will be displayed acknowledging the normalcy of the operation (S213), and the process advances to the step S202. fails to confirm operation (S211: N), a message prompting the operation confirmation will be displayed on the message area 2003 (S212), and the process advances to the step S202. On the other hand, if it succeeds in confirming the operation (S211: Y), a message confirming the connection will be displayed acknowledging the normalcy of the operation (S213), and the process advances to the step S202.

At the step S202, the operation confirmations are repeated on all devices, which have been confirmed the connections of. If there is any item, for which the confirmation is negative (S203: Y), the check mark in the box corresponding to the particular device is removed (S221), and the process proceeds to the next step S204. If there is no negative result (S203: N), the process proceeds straight to the next step S204. The procedures at the steps S202, S203 and S221 are intended for continuing to check the operation status of each device constantly and warn the operator if an abnormality is found in the operation of a device even after it was confirmed the operation of and prevents the operator from advancing to the next screen.

Next, at the step S204, a judgment is made whether the forward step button is pressed. If the forward step button has been pressed (S204: Y), it makes a judgment further where all check boxes have been marked (S231), displays a message to confirm the items if there are any unchecked marks (S232), and proceeds to the step S201. Unless all the check boxes are marked, in other words, unless the operations of a minimum number of devices are all confirmed, the system does not allow the operator to advance to move to the next screen.

On the other hand, if all items are check marked, the process at this screen is terminated. When the process at the connection screen is terminated, the screen advances to the simulation screen.

Figure 11:
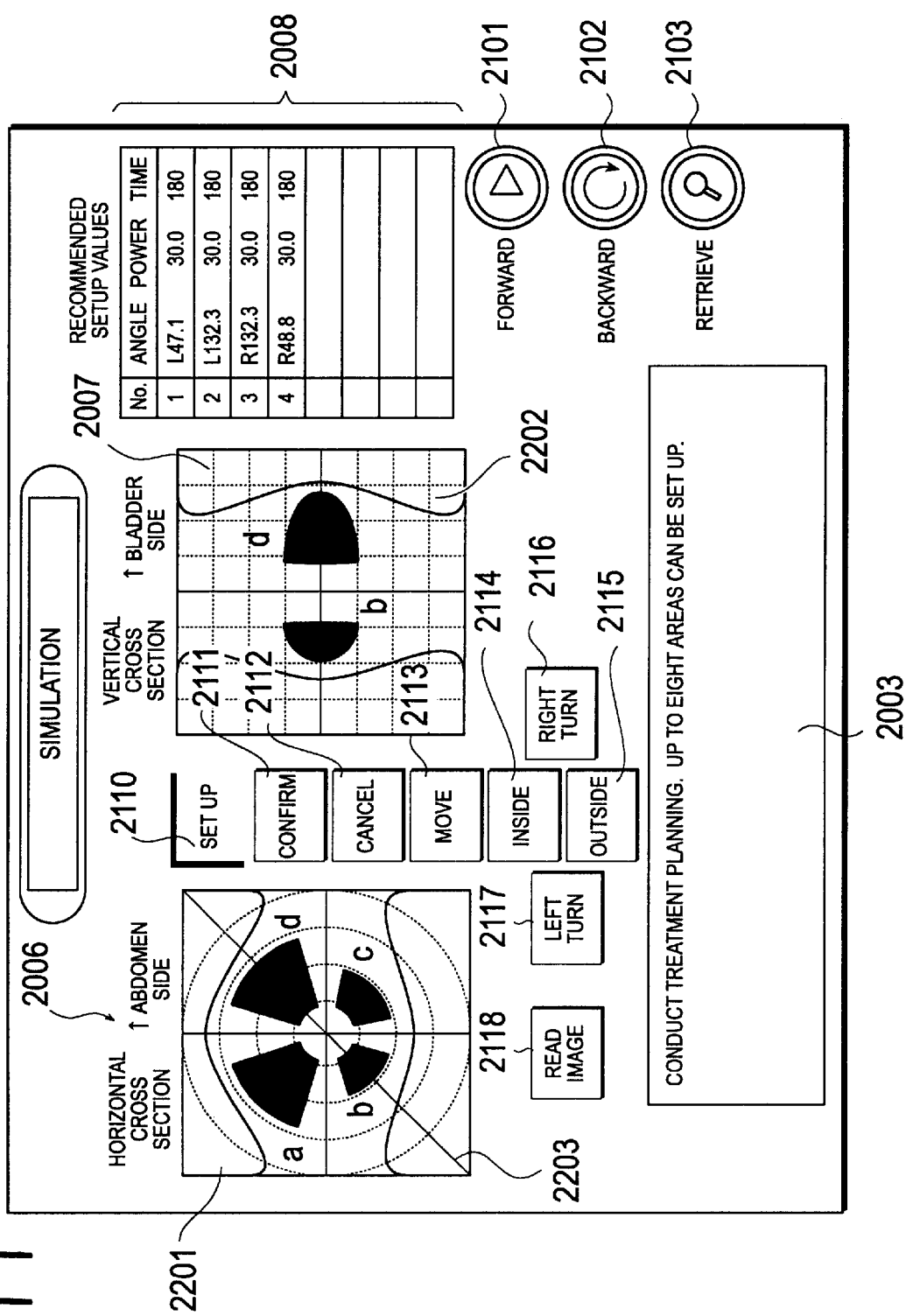
FIG. 11 is a drawing for describing a simulation screen.

The simulation screen consists of, as shown in FIG. 11, the message area 2003, a treatment location horizontal cross section display area 2006, a treatment area vertical cross section display area 2007, a list of recommended setup values display area 2008, a setup button 2110, confirmation button 2111, a cancellation button 2112, a move button 2113, an inside button 2114, an outside button 2115, a right turn button 2116, a left turn button 2117, an image reading button 2118, the forward step button 2101, the backward step button 2102 and a retrieval button 2103.

The treatment location horizontal cross section display area 2006 includes a horizontal cross section image 2201 of a diagnostic image, a vertical cross section location display line 2203 that indicates the vertical cross section location displayed in the treatment location vertical cross section display area 2007, and laser beam irradiation area displays a, b, c and d that shows the laser beam irradiation area. The treatment location vertical cross section display area 2007 includes a vertical cross section image 2202 of the portion shown by the vertical cross section location display line 2203 of the diagnostic image and the laser beam irradiation area displays b and d of said portion (if the position of the vertical cross section location display line 2203 is different, a portion different from the portion indicated in the drawing will, of course, be displayed). Although four laser beam irradiation areas, a, b, c and d are shown in the drawing, up to eight laser beam irradiation areas can be displayed as described later, so that this laser beam irradiation area display can also display up to eight of them. This laser beam irradiation area display will be displayed each time when a laser beam irradiation area is set up. In other words, the display itself does not exist if no laser beam irradiation area is set up.

Figure 12:
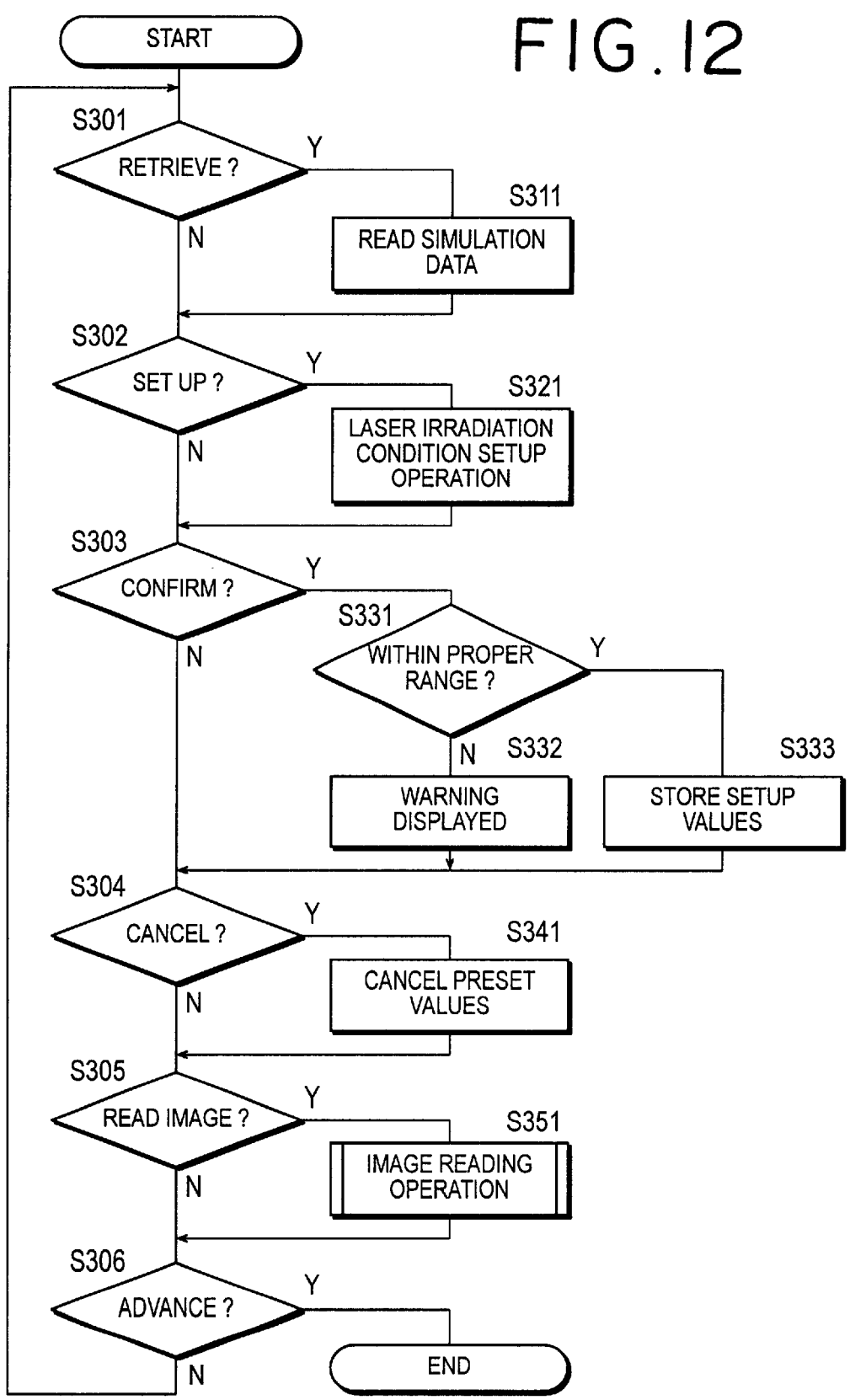
FIG. 12 is a flowchart showing an operation sequence performed on said simulation screen.

FIG. 12 is a flow chart that shows the sequence of various setup operations that are performed from this simulation screen.

First, the simulation screen is displayed and the CPU 231 becomes a status of waiting for an input. When the retrieval button 2103 in the simulation screen is pressed at this point (S301: Y), the system becomes ready for reading the existing simulation data, and the operator retrieves data that are suitable for the lesion to be treated from the existing simulation data (S311). Of the data thus retrieved, the output conditions such as the laser output angle and output energy as well as time (duration) will be displayed in the list of recommended setup values display area 2008, and the laser beam irradiation area displays a, b, c, and d will be displayed in the treatment location horizontal cross section display area 2006 and the treatment location vertical cross section display area 2007.

If the setup button 2110 is pressed (S302: Y), the laser beam irradiation condition setup operation is performed (S321). A new laser beam irradiation condition setup operation is done by touching a desired treatment target area in the treatment location horizontal cross section display area 2006, which causes a new laser beam irradiation area to be set up and said new laser beam irradiation area to be displayed on the screen. However, there is a limit to the number of areas to be set up. In case of this embodiment, the maximum number of laser beam irradiation areas is eight, so that this setup operation is effective until the total number of the laser beam irradiation areas reaches eight.

In order to make a finer adjustment on the laser beam irradiation area, touch the laser beam irradiation area display on the screen to cause it to be in the selected condition, and press the move button 2113. The selected condition is displayed by turning the display color of the touched laser beam irradiation area darker or by changing the display color. Touching an inner button 2114, an outer button 2115, a right turn button 2116, or a left turn button 2117 under this selected condition causes the position, angle, size, and other attributes of the laser beam irradiation area displays a, b, c, and d to change, thus resulting in the adjustment of the position, angle, size, and other attributes of the selected laser beam irradiation area. The laser beam irradiation area is set up in this case with the coordinate center in the treatment location horizontal cross section display area 2006 as a reference point.

The reference point in setting up the laser beam irradiation area can be set up not only at the center of the treatment location horizontal cross section display area 2006 but also at an arbitrary point in said area.

The treatment conditions, which include the irradiation angle, the laser output power, and the laser output time, are displayed in the list of recommended setup values display area 2008 as the treatment conditions of the retrieved simulation data as the simulation data is retrieved as described before. However, it is also possible to set up the treatment conditions arbitrarily (by pressing the setup button). Arbitrary setup of the treatment conditions can be accomplished by touching a desired item to be set up in the list of recommended setup values display area 2008, which causes a software keyboard (refer to FIG. 20) to be displayed on the screen and allows the operator to enter the data using the keyboard. This setup method is also used in the additional setup after the laser beam irradiation.

The setup of the treatment area (laser beam irradiation area) and the treatment condition can be done on up to eight treatment locations from this simulation screen in this embodiment. This depends also on the memory capacity for storing the setup value and lesion image, but it can also be arranged to use a sufficiently large memory capacity to allow to set up more treatment areas.

Figure 13:
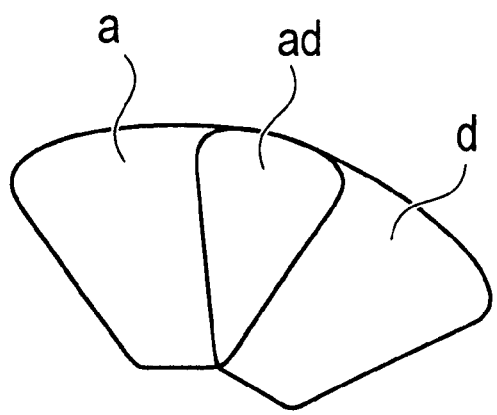
FIG. 13 is a drawing for describing an overlapping of laser beam irradiation areas.

When the confirmation button 2111 is pressed (S303: Y), the system makes a judgment whether the laser beam irradiation conditions (values displayed in the laser beam irradiation area and the list of recommended setup values display area) displayed in the current simulation screen are within the appropriate range (S331). If the laser beam irradiation conditions are judged to be beyond the appropriate range, a warning will be issued (S332). This warning is issued, for example, when the laser beam irradiation output is larger than the safety range, or when the laser beam irradiation regions are overlapping. The laser beam irradiation areas are considered overlapped, for example, when the laser beam irradiation areas "a" and "d" are overlapped as shown in FIG. 13. In this case, the overlapped area "ad" will be irradiated twice, which is not desirable, so that a warning is issued.

If the laser beam irradiation conditions are within an appropriate range, the current setup values will be stored in the memory 232 (S333).

When the cancellation button 2112 is pressed (S304: Y), the display in the laser beam irradiation area will be erased and the values stored in the memory 232 will be erased (S341).

Figure 14A:
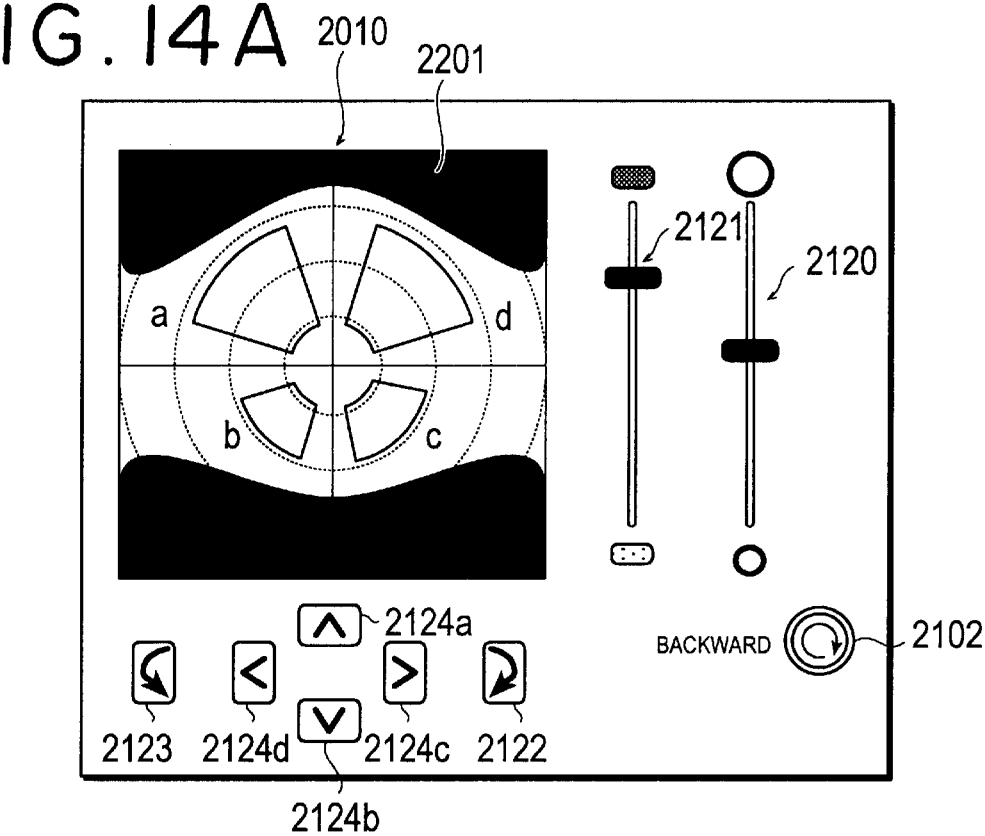
FIG. 14 is a drawing for describing an image reading screen.
Figure 14B:
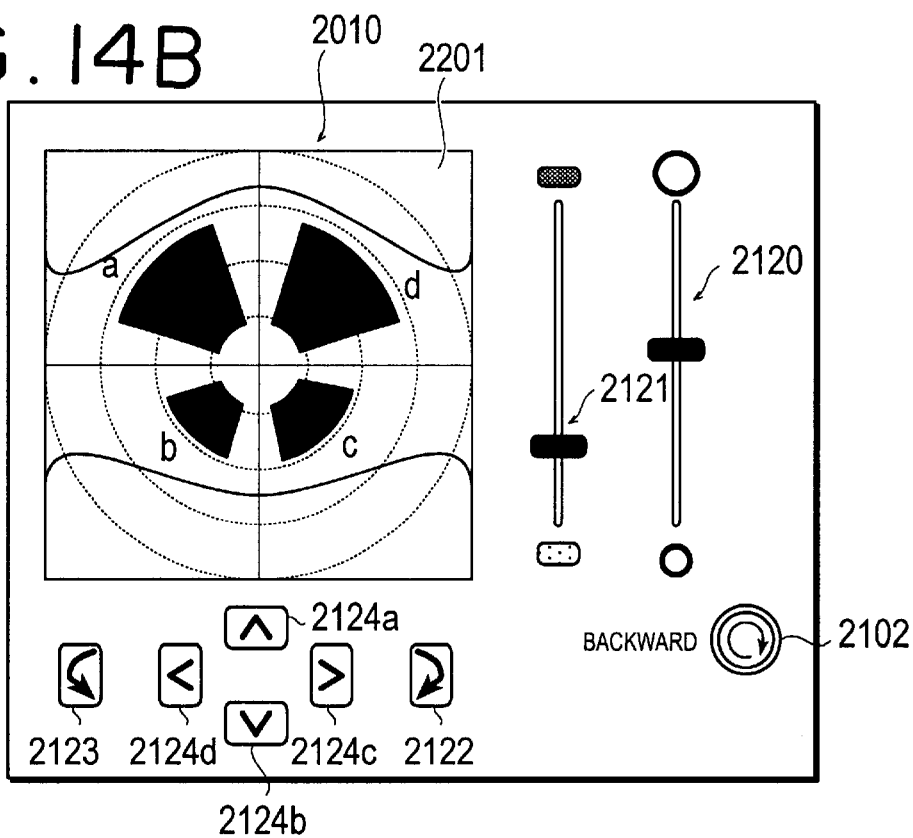

When an image read button 2118 is pressed (S305: Y), the image read operation starts (S351), and the screen switches to the image read adjustment screen shown in FIG. 14. FIG. 14 shows two cases with different image densities, wherein FIG. 14A is with a denser image and FIG. 14B is with a lighter image.

This image read adjustment screen is an interface screen for reading the diagnostic image of the lesion from a FD, etc., overlapping it with the laser beam irradiation area, and adjusting the image density and position. This screen consists of an image display area 2010, an enlarging/reducing bar 2120 of the diagnostic image, a diagnostic image density adjustment bar 2121, a right turn button 2122 for turning the diagnostic image, a left turn button 2123, a upward movement button 2124a for moving the diagnostic image, a downward movement button 2124b, a right movement button 2124c, a left movement button 2124d, and a return button 2102.

Figure 15:
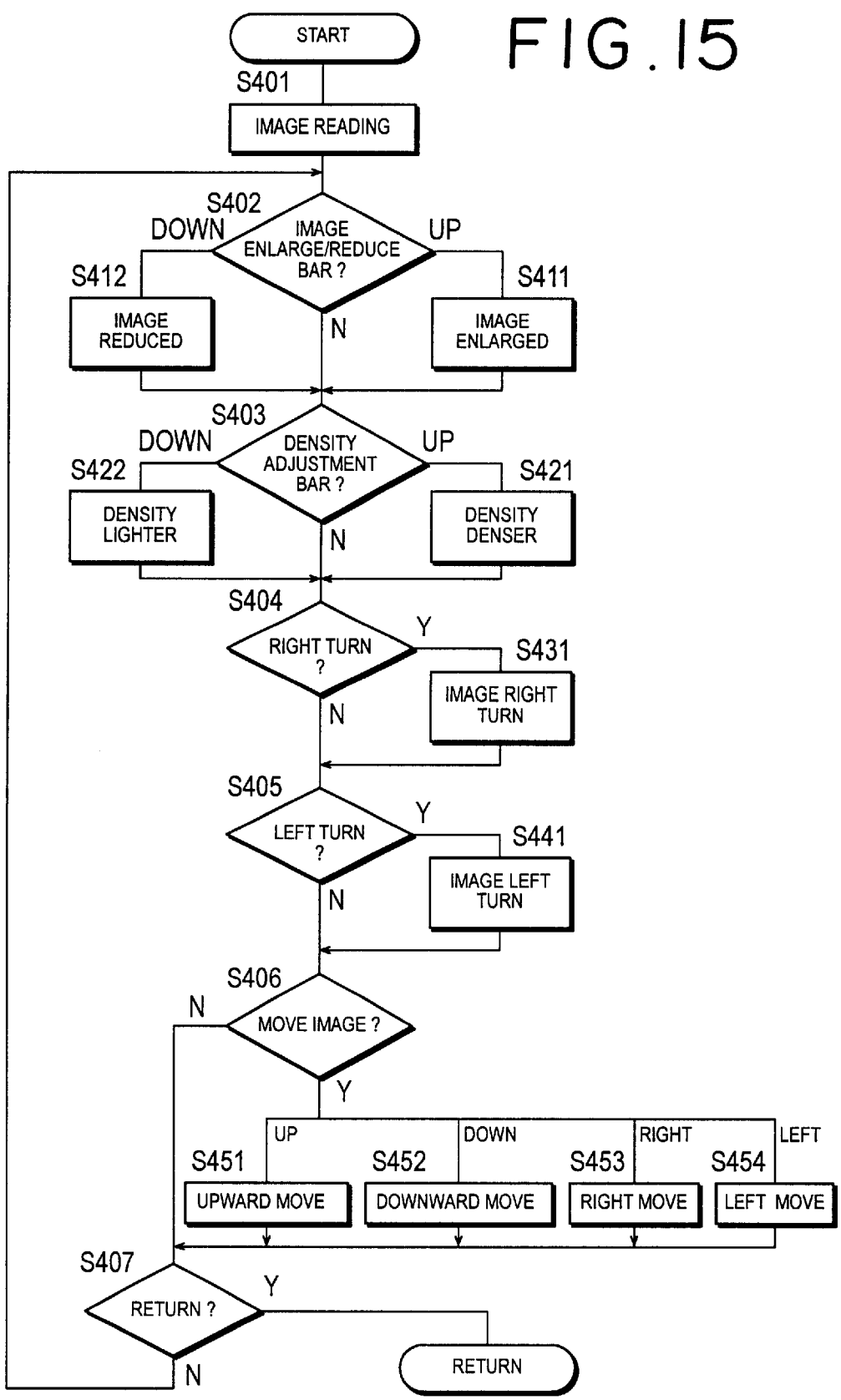
FIG. 15 is a flow chart showing an operation sequence performed on said image reading screen.

FIG. 15 is a flow chart for operation sequences for image reading and image adjustment.

First, the diagnostic image reading from a FD is performed (S401). After having been read, the diagnostic image 2201 will be displayed in the image display area 2010 overlapping the laser beam irradiation area displays a, b, c, and d. The diagnostic image 2201 may be too thin or dense in this case. The center of the laser beam irradiation area may not match with the center of the lesion. The position and the density of the diagnostic image 2201 can be adjusted relative to the laser beam irradiation area displays a, b, c, and d by means of the enlarging/reducing bar 2120, the density adjustment bar 2121, the right turn button 2122, the left turn button 2123, the movement buttons 2124a through 2124d. After reading the image, the screen turns into a waiting state for bar and button inputs.

When the enlarging/reducing bar 2120 is moved upward (S402: up), the diagnostic image 2201 will be enlarged (S411), when it is moved downward (S402: down), the diagnostic image 2201 will be reduced in size (S412), and when it is not moved at all (S402: N), neither enlargement nor reduction occurs.

When the density adjustment bar 2121 is moved upward (S403: up), the density of the diagnostic image 2201 is darkened (S421), when it is moved downward (S403: down), the density of the diagnostic image 2201 is lightened (S422), and when it is not moved at all (S403: N), the density of the diagnostic image 2201 stays unchanged. FIG. 14 shows this density change of the diagnostic image 2201. As can be seen from FIG. 14A, when the density adjustment bar 2121 is moved upward, the density of the diagnostic image 2201 increases relative to the laser beam irradiation area displays a, b, c, and d, so that it becomes easier for the operator to read the diagnostic image 2201. On the other hand, when the density adjustment bar 2121 is moved downward, the density of the diagnostic image 2201 decreases relative to the laser beam irradiation area displays a, b, c, and d, so that it becomes easier for the operator to read the laser beam irradiation area displays a, b, c, and d. Thus, the operator can adjust the image to make it more readable.

When the right turn button 2122 is pushed (S404: Y), the diagnostic image 2201 turns right (S431). When the left turn button 2123 is pushed (S405: Y), the diagnostic image 2201 turns left (S441).

When the upward move button 2124a is pushed (S406: up), the diagnostic image 2201 moves upward (S451). When the downward move button 2124b is pushed (S406: down), the diagnostic image 2201 moves downward (S452). When the rightward move button 2124c is pushed (S406: right), the diagnostic image 2201 moves right (S453). When the leftward move button 2124d is pushed (S406: left), the diagnostic image 2201 moves left (S454).

When the return button is pressed (S407: Y), the process returns to the simulation screen (FIG. 11).

Although it is arranged in such a way as to move or enlarge/reduce the retrieved diagnostic images, it is also possible to move or enlarge/reduce relative to the laser beam irradiation area relative to the diagnostic image.

When the advance pushbutton 2101 is pressed in the simulation screen (FIG. 12, S306), the setup in this simulation screen will be terminated and the process will move to the next irradiation target selection screen.

The irradiation target selection screen is a screen for selecting the irradiation area for conducting laser beam irradiation, and selecting the laser beam irradiation location here causes the process to move to the next irradiation screen.

Figure 16:
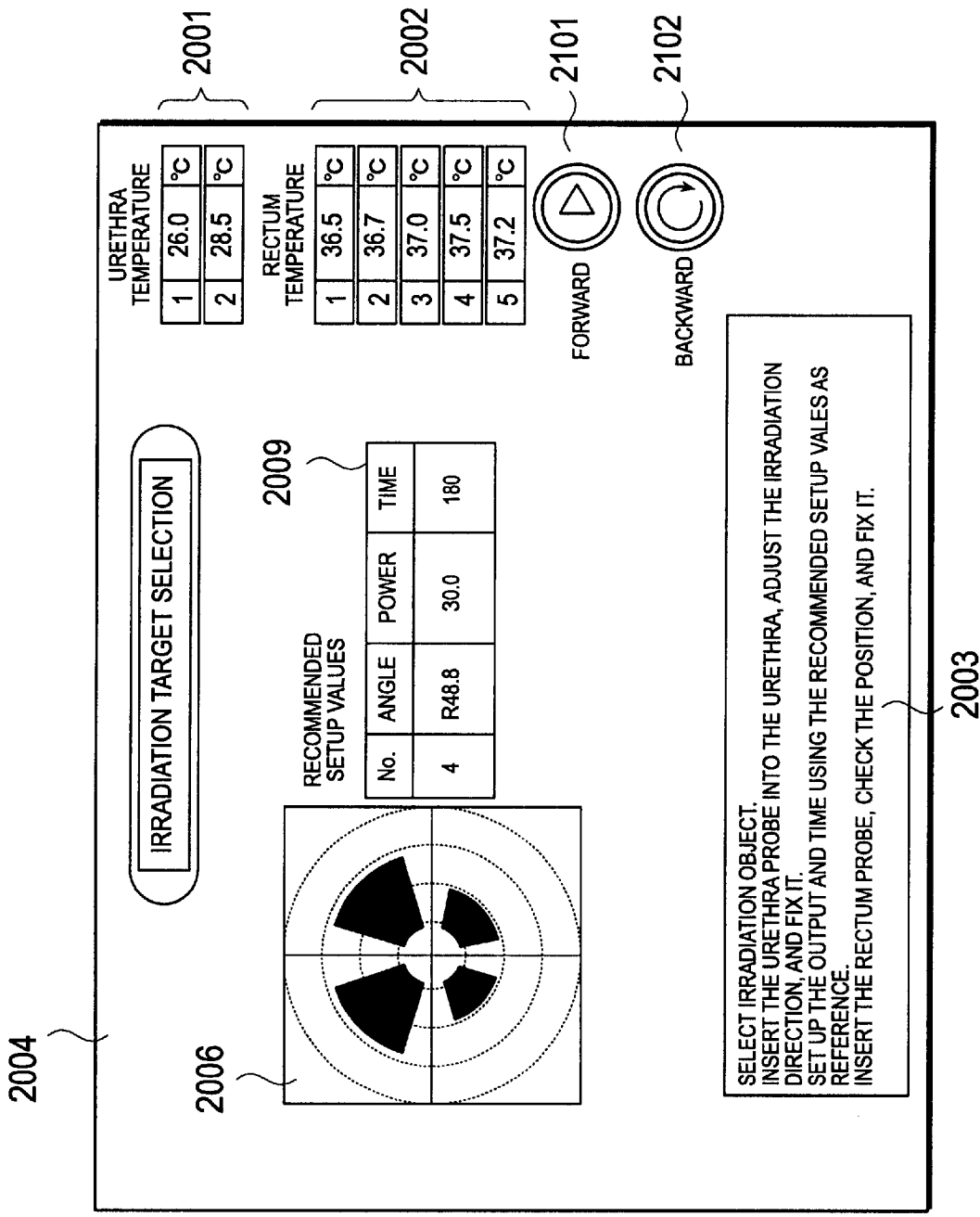
FIG. 16 is a drawing for describing an irradiation target selection screen.

The irradiation target selection screen consists of, as shown in FIG. 16, the urethra temperature display area 2001, the rectum temperature display area 2002, the message area 2003, the treatment location horizontal cross section display area 2006, a recommended value display area 2009, the forward step button 2101, and the backward step button 2102.

Figure 17:
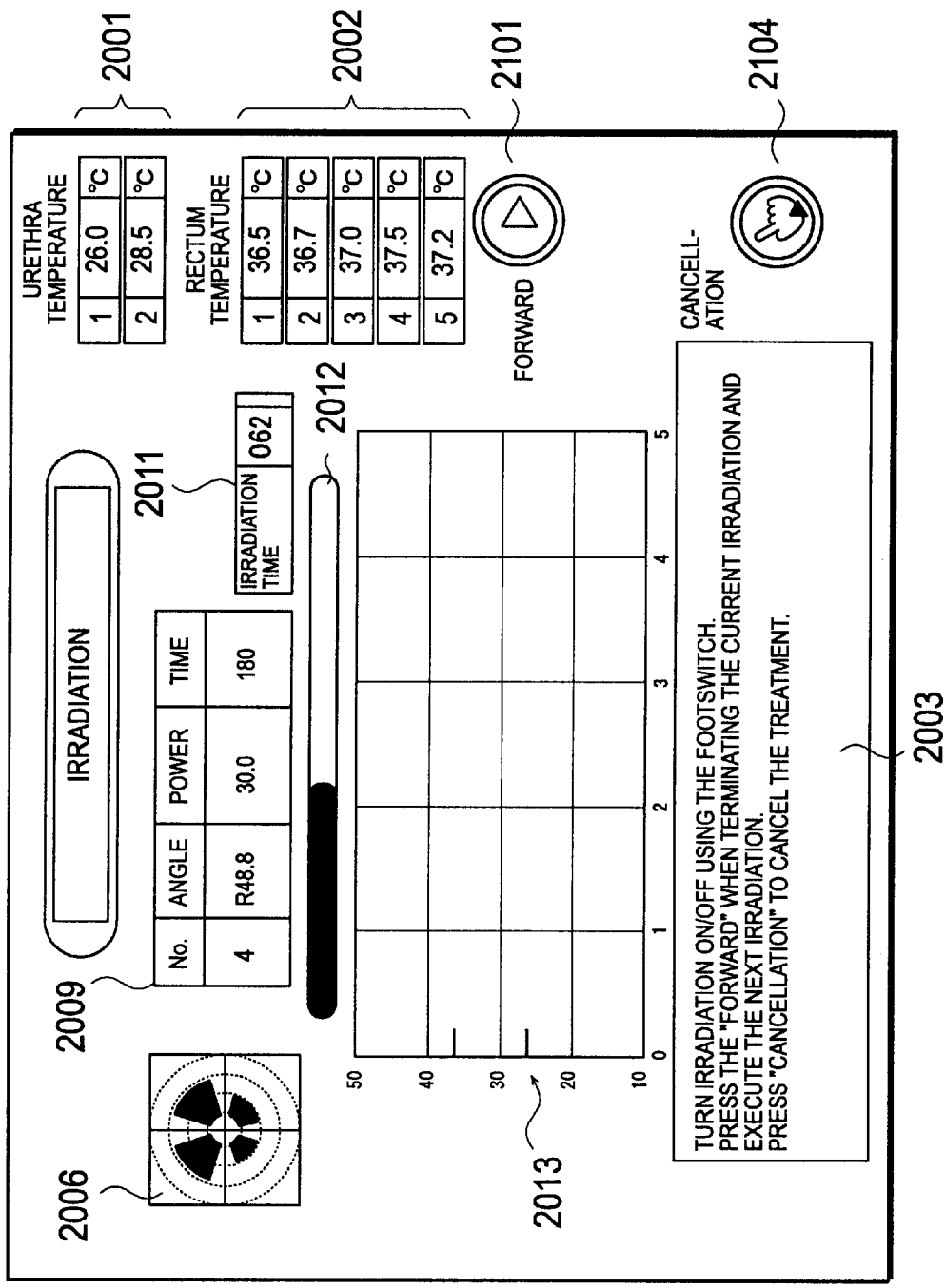
FIG. 17 is a drawing for describing an irradiation screen.

The irradiation screen consists of, as shown in FIG. 17, the urethra temperature display area 2001, the rectum temperature display area 2002, the message area 2003, the treatment location horizontal cross section display area 2006, a recommended value display area 2009, an irradiation time display area 2011, an irradiation time bar graph display area 2012, a display area 2013 for showing the changes in the urethra temperature and the rectum temperature during treatment, a forward step button 2101, and a cancellation button 2104.

Figure 18:
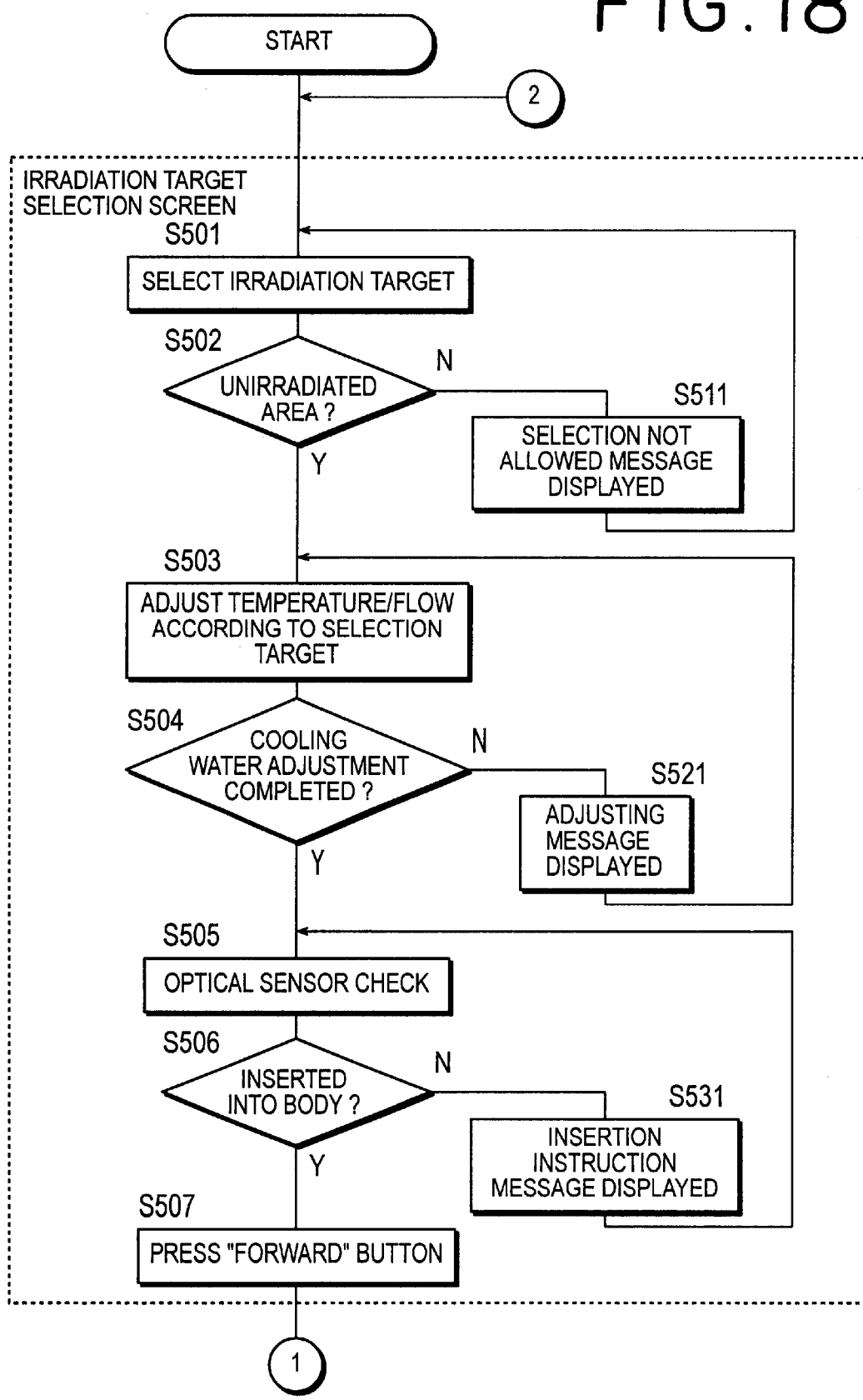
FIG. 18 is a flow chart showing an operation sequence performed on said irradiation screen starting from said irradiation target selection.
Figure 19:
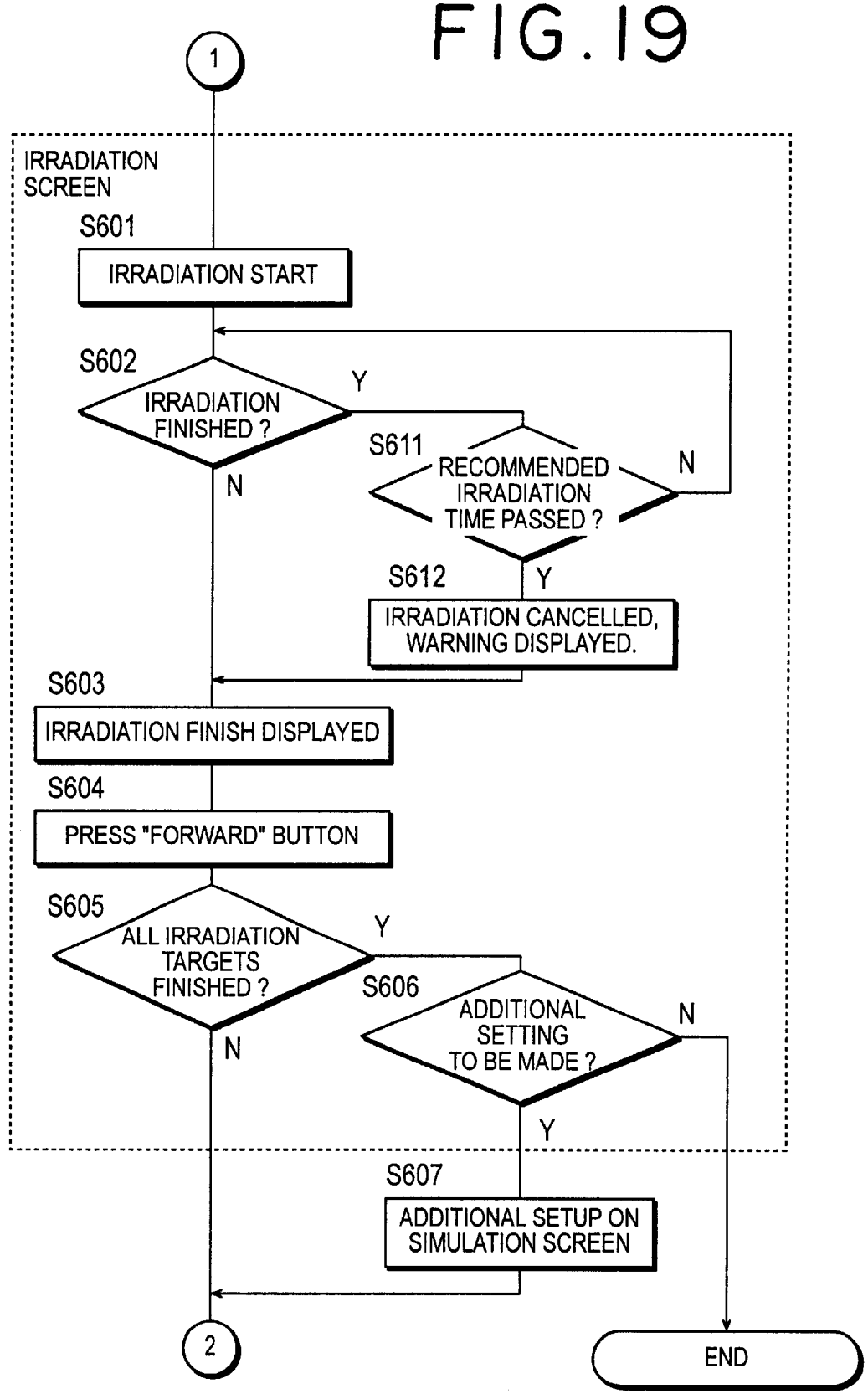
FIG. 19 is a flowchart showing an operation sequence after FIG. 18 performed on said irradiation screen starting from said irradiation target selection.

FIG. 18 and FIG. 19 jointly indicate a flow chart showing the operation procedures in the irradiation target selection screen and the irradiation screen.

First, touching either of the irradiation area displays on the irradiation target selection screen selects one of them as a laser beam irradiation area (S501).

Next, a judgment will be made whether the selected laser beam irradiation area is an unirradiated area (S502). This judgment is a process for preventing an already irradiated area from being irradiated again during the process of selecting an area for irradiation. All the areas, which have been irradiated, are recorded for this purpose, and a message of selection disapproval will be displayed if an area which has already been irradiated is selected (S511).

Next, if a proper laser beam irradiation is selected, the temperature and flow of the cooling water will be automatically adjusted depending on the selected target (S503). Optimum temperature and flow of the cooling water will be automatically selected from the already inputted laser irradiation time and output in this embodiment. The cooling water temperature should preferably be 0 through 37 in order to reduce the risk of damages on the laser emission part 122 and the irradiated surface of the tissue due to the laser beam irradiation, or more preferably 8 through 25 in order to reduce the risk of cold injuries and yet have a high chilling efficiency at the same time. It is preferable to use a disinfected liquid, such as purified water or normal saline solution as the refrigerant in order to minimize the operator's burden. It is also possible to have an arrangement to be able to adjust the temperature and flow of the refrigerant arbitrarily.

Next, a judgment is made whether the temperature and flow of the cooling water have become proper values (S504). The display will be shown until it is determined that the cooling water has been adjusted to the correct values (S521).

After the temperature and flow of the cooling water have become proper values, the signal of the optical sensor 114 is checked (S505). If it is detected by means of the optical sensor that the insertion part 121 of the laser irradiation unit 1 is not inserted into the body of the laser beam irradiation target (S506: N), a display will be made to prompt the insertion part 121 to be inserted in the body of the laser beam irradiation target (S531).

If on the other hand, the insertion part 121 has been inserted into the body of the laser beam irradiation target (S506: Y), it advances to the irradiation screen when the advance button 2101 is pressed (S507).

The irradiation screen displays a message in the message area prompting the operator to conduct the laser beam irradiation (S601). At this time, it is recorded that the laser beam irradiation is executed in this area. Also, the laser beam irradiation time counting starts at the same time.

The irradiation screen also displays a software keyboard (refer to FIG. 20) when the recommended value display area 2009 is touched and allows the operator to enter the laser beam irradiation conditions. This function is provided to allow the operator to change the laser beam irradiation conditions instantaneously just before the start of the irradiation.

Next, a judgment is made whether the laser irradiation is completed (S602). This judgment will be made based on whether the footswitch is turned off. If the laser beam irradiation has not been completed, a judgment will be made whether the recommended irradiation time is up (S611). If the recommended irradiation time is not up yet (S611: N), the process returns to the step S602, and the laser irradiation will be continued. On the other hand, if the recommended laser irradiation time is up (S611: Y), the laser irradiation will be terminated forcibly (S612).

If the laser irradiation is completed, a message will be displayed announcing that the irradiation is completed (S603). When the advance pushbutton is pressed (S604), a judgment is made as to whether the laser beam irradiations are completed to all the irradiation targets (S605). If it is judged that the laser beam irradiations to all the irradiation targets have been completed (S605: Y), a message will be displayed asking whether the operator wishes to set up additional irradiations. If the operator selects to set up additional irradiations (S606: Y), the process returns to the simulation screen allowing the additional setup (S607). If the operator selects to terminate the irradiation (S606: N), the process terminates the process and advances to the data input screen.

If the cancellation button 2104 is pressed on the irradiation screen, the laser beam irradiation will be stopped on the spot. It is of course possible to stop the laser beam irradiation by turning the footswitch off. If the cancellation pushbutton 2104 is pressed, the process advances to the data input screen.

When the process returns to the irradiation target selection screen, it continues on the process from the step S501.

Figure 20:
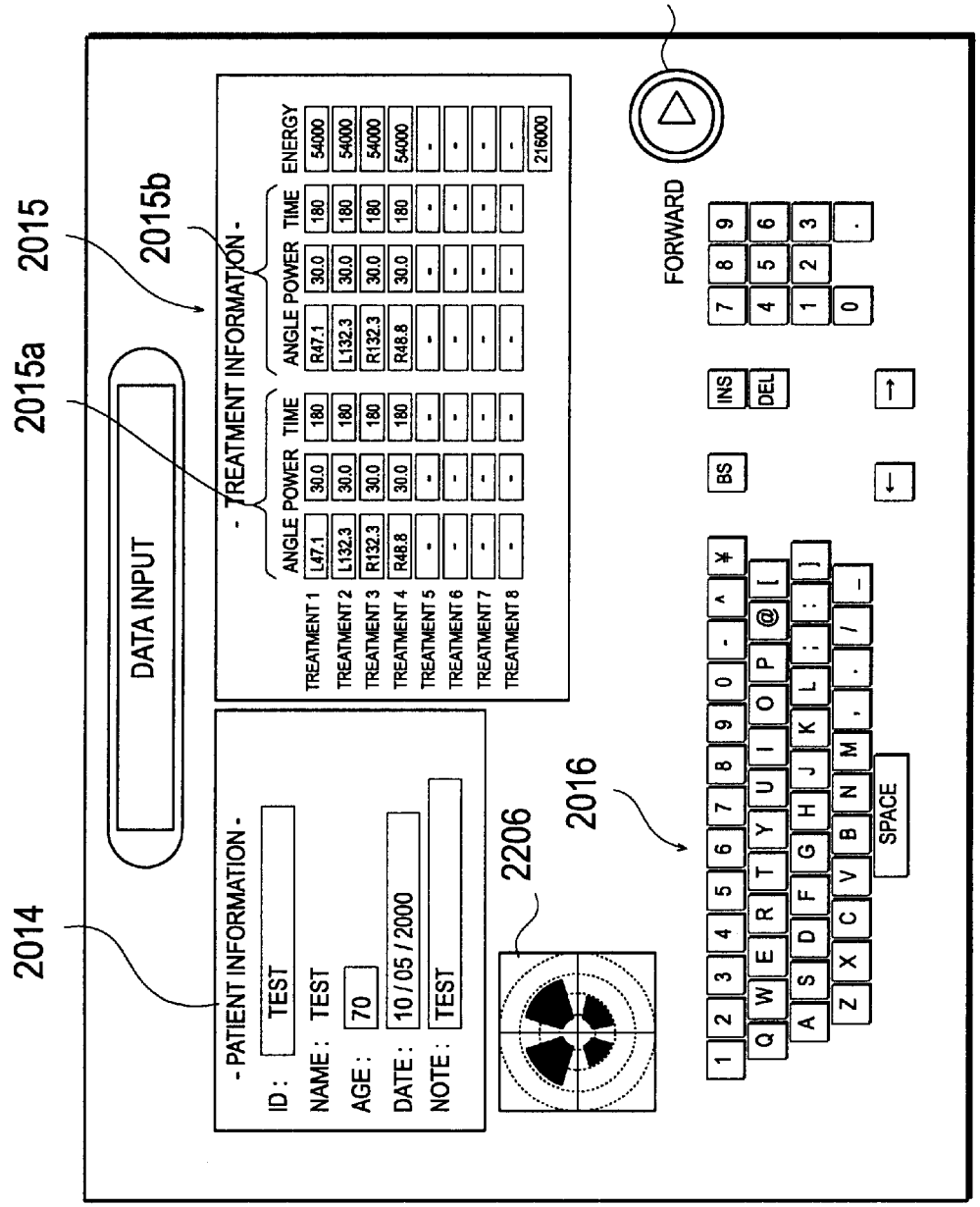
FIG. 20 is a drawing for describing a data input screen.

The data input screen consists of, as shown in FIG. 20, a patient information input area 2014, a treatment information input area 2015, a software keyboard 2016, a reduced treatment area horizontal cross section display area 2206, and a forward step pushbutton 2101.

The data input screen allows the operator to input the patient's name, age and other information from the patient information input area 2014 using the software keyboard 2016.

The treatment input area 2015 displays in a recommended value display area 2015a the recommended values of the laser beam irradiation conditions set up in the simulation screen and it provides an execution value input area 2015b on the right side to allow the operator to input the actually used laser beam irradiation conditions into the execution value input area 2015b using the software keyboard 2016. This is to accommodate for a last minute change of the laser beam irradiation conditions from the irradiation conditions set up at the simulation screen. The last column on the treatment information input area 2015 shows the automatically calculated total energy (laser output power×time) delivered by the irradiation.

When the forward step pushbutton 2101 is pressed on this data input screen, the process advances to the next output screen.

Figure 21:
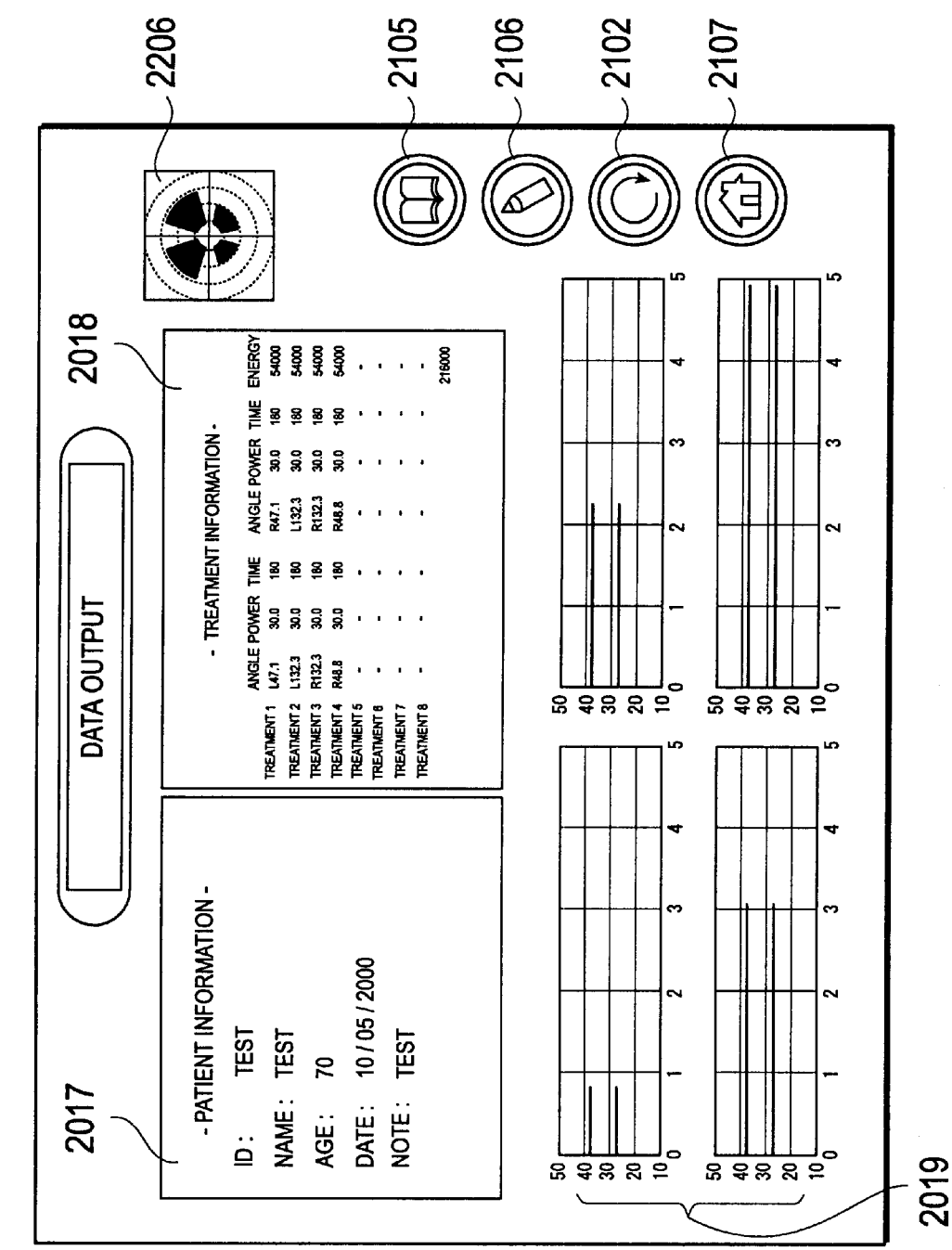
FIG. 21 is a drawing for describing a data output screen.

The data output screen consists of, as shown in FIG. 21, a patient information display area 2017, a treatment information display area 2018 for displaying the actually applied laser beam irradiation conditions, a reduced graph display are 2019 for display the graph for each treatment, the reduced treatment location horizontal cross section display area 2206, a page switching button 2105, a data storage button 2106, the return button 2102, and a termination button 2107.

Figure 22:
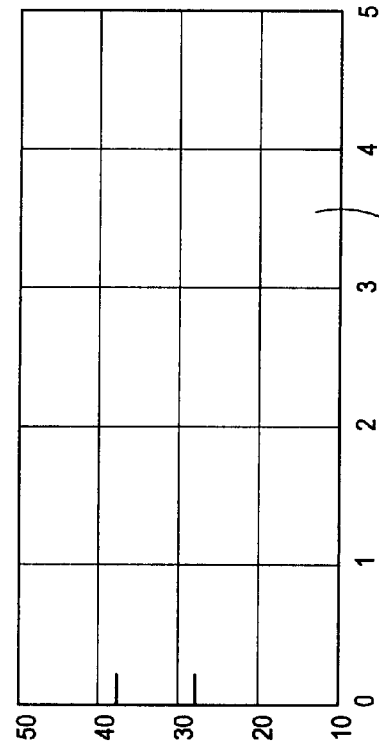
FIG. 22 is a drawing for describing a case where a graph display is enlarged on said data output screen.

The data output image screen displays the patient's data based on the stored patient's information data previously entered into the data input screen. The reduced graph display are 2019 can also enlarge an arbitrary graph. For example, touching a desired graph will cause said graph to be displayed in an enlarged size in the graph display area 2013 as shown in FIG. 22.

Therefore, it is possible to display an arbitrary treatment data of an arbitrary patient on the data input screen and the data output screen. It is of course possible to print out the data displayed on the data output screen by a printer or output to a FD in a format recorded as data.

Those are the operations of the treatment mode in this embodiment.

Since all of the setup and operation instructions can be made from the graphical user interface displayed on the touch panel display, the operator can easily make the treatment planning including complex laser beam irradiation conditions.

The above description of the embodiment is not intended to restrict the scope of the invention and various modifications are possible within the technical thought of this invention.

For example, it is possible to add a process of confirming the patient's data to the treatment mode of the above embodiment.

Figure 23:
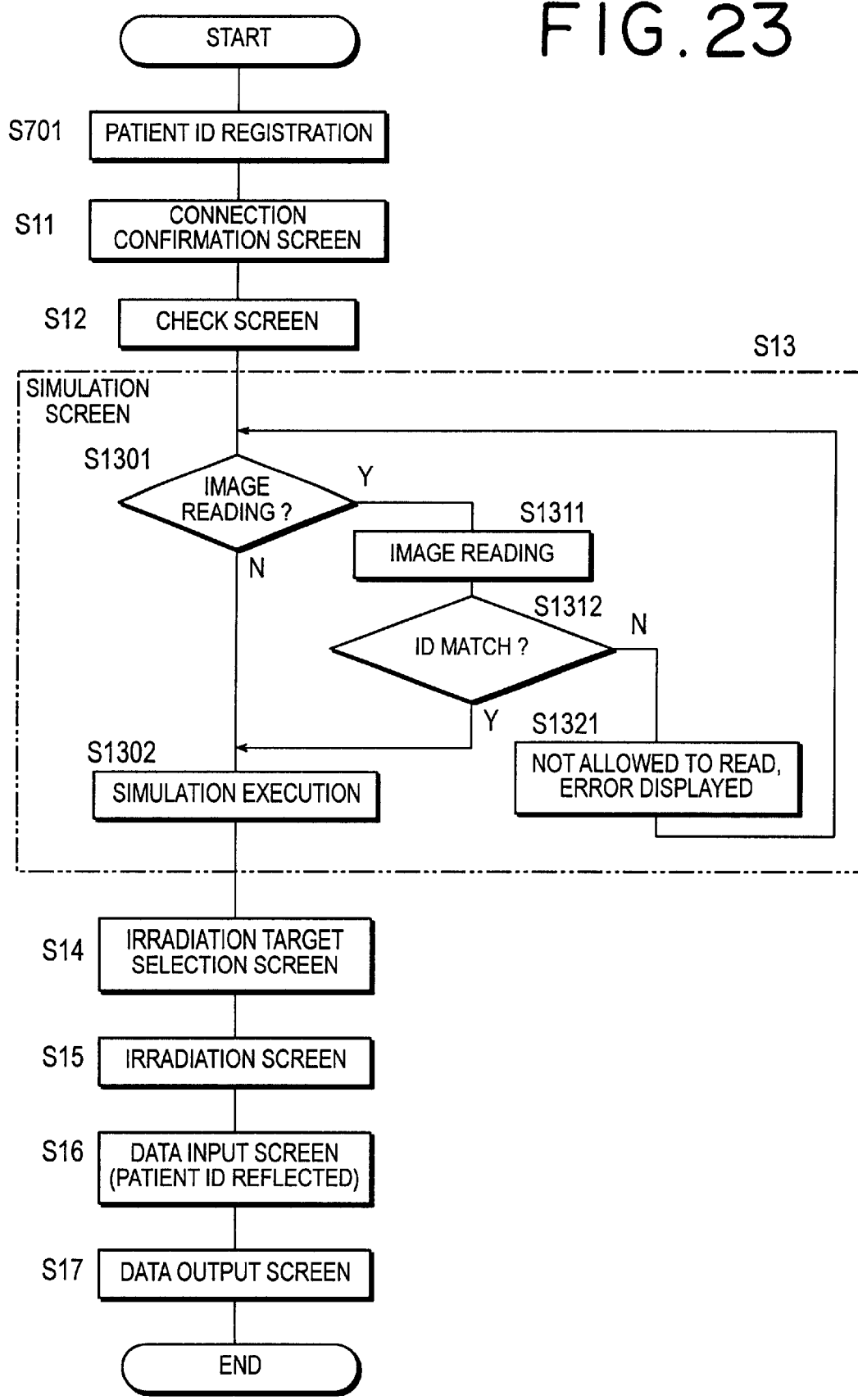
FIG. 23 is a flow chart showing a screen transition in a format using a patient's ID in another embodiment and a sequence performed for confirming the ID.

This is done, as shown in FIG. 23, by first registering the patient's ID information individually set up for each patient in the treatment mode (S701). The patient's ID information can be either a combination of the patient's name, age, date of birth, medical record number, etc., or can be simply a number or code to identify the patient, or can be the patient's finger prints.

Once in the treatment mode, the process goes to the simulation screen (S13) passing through the connection confirmation screen (S11) and a check screen (S12). During the retrieval of the patient's diagnostic image on the simulation screen, a confirmation is made whether the patient's ID previously registered match with the patient's diagnostic image data. In order to do this, first as shown in the diagram, a judgment is made whether the patient's image should be read (S1301). If it is determined to read the image here (S1301: Y), the image will be read (S1311), and a judgment is made whether the patient's ID included in the patient's information in the retrieved image data match with the ID of the patient registered previously (S1312). If the patient's IDs do not match, an error message will be issued as a read failure (S1321), and the process will return to the step S1301. On the other hand, if the patient's IDs match, the simulation will be performed using the retrieved image (S1302). The simulation process here is the same as the one described before for the simulation screen.

After that, the process proceeds, as in the previous embodiment, to the irradiation target selection screen (S14), the irradiation screen (S15), the data input screen (S16), and the data output screen (S17) in that order. It is also possible to arrange the patient's data to be entered into the input screen automatically according to the patient's ID.

This way the thermal treatment patient's data can be read securely.

Figure 24:
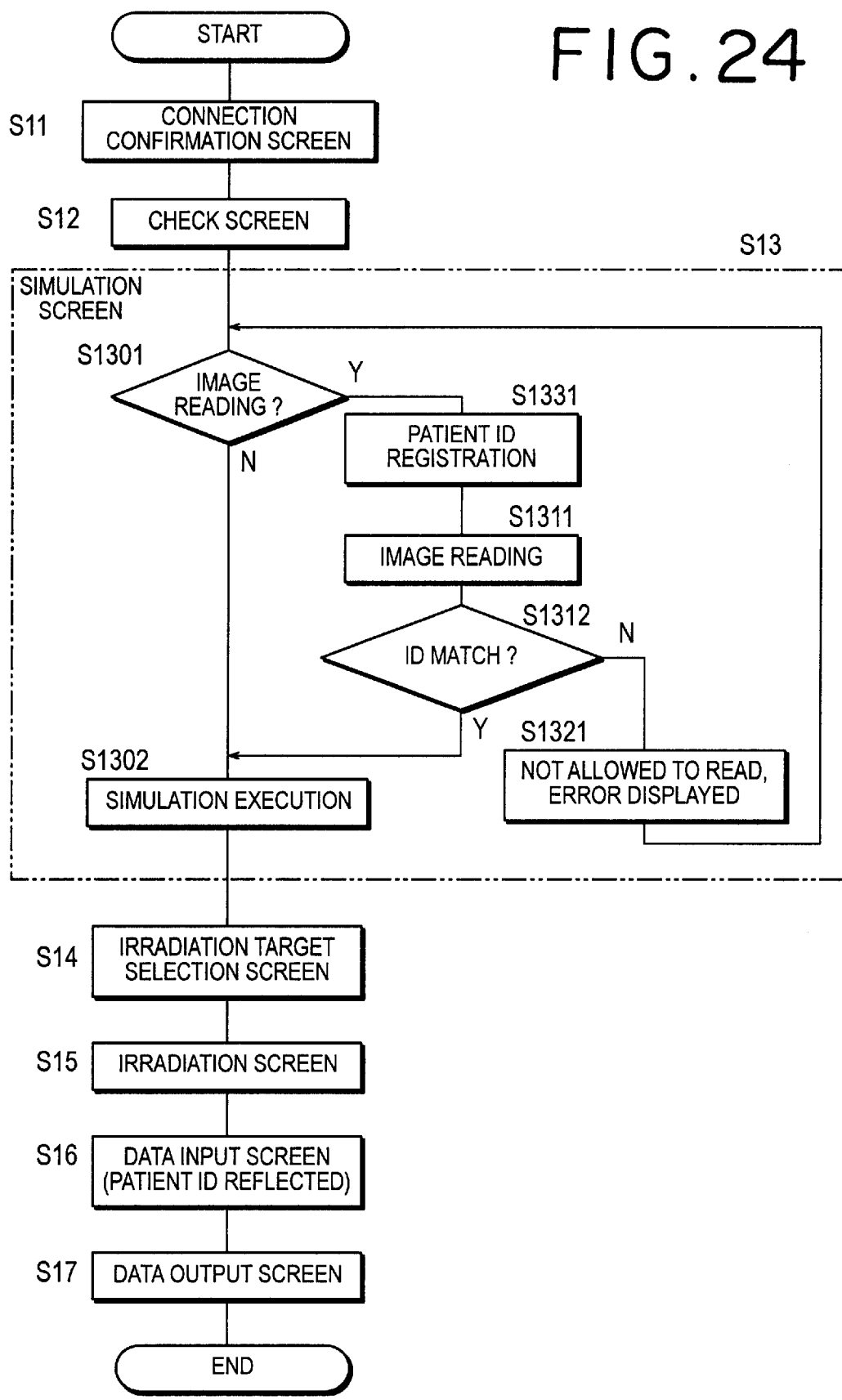
FIG. 24 is a flowchart showing an operation sequence in a case where the confirmation of the patient's ID is performed in another format.

As a modification to this process, it is also possible to register the patient's ID (S1331) as shown in FIG. 24 after making a judgment whether the image reading should be made on the simulation screen (S1301), and then read the image data (S1311), make a judgment to see whether the registered patient's ID matches with the patient's ID on the retrieved image data (S1312), and display an error message if they don't match (S1321), or execute the simulation if they match (S1302). In case of FIG. 24, all other processes are the same as in the previous embodiment so that their descriptions are not repeated here.

The application of this invention is not limited the irradiation of laser beams, but rather it can be applied to the irradiations of other forms of energies such as microwaves, radio frequency and ultrasonic waves as well.

Also, although the above description was based on the assumption that the prostate is the organism to be treated by the thermal treatment, the target of the invention is not limited to it but rather include all kinds of tissues that can absorb energies from the cavities in the body such as blood vessels, digestive tubes (esophagus, bowel, etc.), abdominal cavities, etc., or from the body surface to be treated thermally.

As can be seen from the above, the invention provides a thermal treatment apparatus that allows the operator to set up the thermal treatment plan, i.e., the setup of the energy irradiation area, irradiation output, and irradiation time (duration) easily and securely.

What is claimed is:

1. A thermal treatment apparatus for thermally treating by irradiating living bodies with energy comprising:
    an energy supplying means for supplying energies for treatment;
    an energy irradiating means for irradiating living bodies with energies supplied;
    a treatment planning means for setting up treatment areas to be irradiated with energies as treatment area information;
    a setup means for setting up treatment conditions based on treatment area information;
    an image information input means for inputting image information for diagnosis;
    an information overlaying means for overlaying the setup treatment area information on the input image information;
    an information manipulating means for manipulating at least one of the treatment area information or the image information; and
    said energy irradiating means including an elongated insertion part adapted to be inserted into a living organism and an emission part installed in said elongated insertion part to emit energy, said elongated insertion part including moving means for moving a position of said emission part in a longitudinal direction of said elongated insertion part and angle changing means for changing an emission angle of the energy emitted by the emission part in accordance with movement of the emission part by said moving means.

2. The thermal treatment apparatus according to claim 1 further comprising:
    an input means for inputting patient information;
    a comparison means for comparing patient information included in said image information with the inputted patient information; and
    a warning means for warning when said patient information included in said image information does not match with the inputted patient information.

3. The thermal treatment apparatus according to claim 1 further comprising:
    a changing means for changing treatment conditions set up by said setup means, and
    a warning means for warning when a change amount of the treatment conditions exceeds a predetermined range.

4. The thermal treatment apparatus according to claim 1 further comprising:
    a treatment information reading means for reading the treatment area information set up by said treatment planning means and the treatment conditions set up by said setup means; and
    a treatment information change means for changing the treatment area information and the treatment conditions read by said treatment information reading means.

5. The thermal treatment apparatus according to claim 1 further comprising:
    an energy irradiation time measuring means for measuring the time said energy irradiation means irradiated living bodies with energy; and
    a stopping means for stopping the energy irradiation according to said energy irradiation means when an actual energy irradiation time exceeds an energy irradiation time set up for said treatment condition based on a comparison of the actual energy irradiation time measured by the energy irradiation time measuring means and the energy irradiation time set up for said treatment condition.

6. The thermal treatment apparatus according to claim 1, wherein
    said treatment planning means, said setup means, said image information input means, and said information overlaying means are equipped with graphical user interface screens, and
    said graphical user interface screens consist of several setup screens, with completion of all necessary setup of one of the setup screens being required to proceed to a next one of the setup screens.

7. The thermal treatment apparatus according to claim 6, wherein said graphical user interface screens are displayed on a touch panel display.

8. The thermal treatment apparatus according to claim 1, wherein
    the treatment condition set up in said setup means includes at least one of the following items: number of energy irradiation(s), energy irradiation direction, output power of energy, output time of energy, coolant temperature when a coolant is used, coolant flow amount when a coolant is supplied, and motion speed when said emission part is moved.

9. The thermal treatment apparatus according to claim 8 further comprising:
    a control means for controlling, according to the treatment condition set up in said setup means, at least one of the following items: the number of energy irradiation(s), the energy irradiation direction, the output power of energy, the output time of energy, the coolant temperature when a coolant is used, the coolant flow amount when a coolant is supplied, and the motion speed when said emission part is moved.

10. The thermal treatment apparatus according to claim 1, wherein said energy supply means is a laser apparatus.

11. The thermal treatment apparatus according to claim 1, wherein said insertion part has a lumen for inserting image input means for inputting images.

12. The thermal treatment apparatus according to claim 1, wherein said insertion part further comprises: a cooling means for cooling a vicinity of said mission part.

13. The thermal treatment apparatus according to claim 1, wherein said treatment planning means sets up irradiation areas of energy of the treatment area information by establishing a coordinate of a single reference point.

14. The thermal treatment apparatus according to claim 13, wherein said reference point can be set up at an arbitrary position within a predetermined area.

15. The thermal treatment apparatus according to claim 13, further comprising: an overlapping area warning means which issues a warning when overlapping area exists in a preset energy irradiation area.

16. The thermal treatment apparatus according to claim 1, wherein said information manipulating means adjusts at least one of the following items: position adjustment, angle adjustment, scaling adjustment and density adjustment.

17. A thermal treatment apparatus for thermally treating by irradiating living bodies with energy comprising:
   an energy supplying means for supplying energies for treatment;
   an energy irradiating means for irradiating living bodies with energies supplied;
   a treatment planning means for setting up at least two treatment areas to be irradiated with energies as treatment area information;
   a selection means for arbitrarily selecting areas to be treated among preset treating areas;
   a setup means for setting up treatment conditions based on the selected treatment areas;
   said energy irradiating means including an elongated insertion part adapted to be inserted into living organisms and an emission part installed in said elongated insertion part to emit energy, said elongated insertion part including moving means for moving a position of said emission part in the longitudinal direction of said elongated insertion part, and angle changing means for changing an emission angle of the emission energy in accordance with motion of the emission part by said moving means.

18. The thermal treatment apparatus according to claim 17 further comprising:
   a changing means for changing the treatment conditions set up by said setup means; and
   a warning means for issuing a warning when a change amount of the treatment conditions exceeds a predetermined range.

19. The thermal treatment apparatus according to claim 17 further comprising:
   a treatment information reading means for reading the treatment areas set up by said treatment planning means and the treatment conditions set up by said setup means; and
   a treatment information changing means for changing the treatment areas and the treatment conditions read out by said treatment information reading means.

20. The thermal treatment apparatus according to claim 17 further comprising:
   an energy irradiation time measuring means for measuring the time said energy irradiation means irradiated living bodies with energy; and
   a stopping means for stopping the energy irradiation according to said energy irradiation means when an actual energy irradiation time exceeds an energy irradiation time set up for said treatment condition based on comparison of the actual energy irradiation time measured by the energy irradiation time measuring means and the energy irradiation time set up for said treatment condition.

21. The thermal treatment apparatus according to claim 17, wherein
   said treatment planning means and said setup means are equipped with graphical user interface screens, and
   said graphical user interface screens consist of several setup screens, with completion of all necessary setup of one of the setup screens being required to proceed to a next one of the setup screens.

22. The thermal treatment apparatus according to claim 21, wherein said graphical user interface screen is displayed on a touch panel display.

23. The thermal treatment apparatus according to claim 17, wherein
   the treatment condition set up in said setup means includes at least one of the following items: number of energy irradiation(s), energy irradiation direction, output power of energy, output time of energy, coolant temperature when a coolant is used, coolant flow amount when a coolant is supplied, and motion speed when said emission part is moved.

24. A The thermal treatment apparatus according to claim 23 further comprising:
   a control means for controlling, according to the treatment condition set up in said setup means, at least one of following items: the number of energy irradiation(s), the energy irradiation direction, the output power of energy, the output time of energy, the coolant temperature when a coolant is used, the coolant flow amount when a coolant is supplied, and the motion speed when said emission part is moved.

25. The thermal treatment apparatus according to claim 17, wherein said energy supply means is a laser apparatus.

26. The thermal treatment apparatus according to claim 17, wherein said insertion part has a lumen for inserting image input means for inputting images.

27. The thermal treatment apparatus according to claim 17, wherein said insertion part further comprises: a cooling means for cooling a vicinity of said emission part.

28. The thermal treatment apparatus according to claim 17, wherein said treatment planning means sets up irradiation areas of energy of the treatment area information by establishing a coordinate of a single reference point.

29. The thermal treatment apparatus according to claim 28, wherein said reference point can be set up at an arbitrary position within a predetermined area.

30. The thermal treatment apparatus according to claim 28, further comprising: an overlapping area warning means which issues a warning when overlapping area exists in a preset energy irradiation area.

31. The thermal treatment apparatus according to claim 17 further comprising:
   a recording means for recording the areas where energy irradiations are executed among the treatment areas set up by said treatment planning means, wherein
   said selection means prevents already irradiated areas recorded in said recording means from being selected.

32. A thermal treatment apparatus for thermally treating by irradiating living bodies with energy comprising:

an energy supplying means for supplying energies for treatment;

an energy irradiating means for irradiating living bodies with energies supplied;

a treatment planning means for setting up treatment areas to be irradiated with energies as treatment area information;

a setup means for setting up treatment conditions based on treatment area information;

an image information input means for inputting image information for diagnosis;

an information overlaying means for overlaying the setup treatment area information on the input image information; and an information manipulating means for manipulating at least one of the treatment are information or the image information, wherein said treatment planning means sets up irradiation areas of energy of the treatment area information by establishing a coordinate of a single reference point which can be set up at an arbitrary position within a predetermined area.

33. A thermal treatment apparatus for thermally treating by irradiating living bodies with energy comprising:

energy supplying means for supplying energies for treatment;

energy irradiating means for irradiating living bodies with energies supplied;

treatment planning means for setting up treatment areas to be irradiated with energies as treatment area information;

setup means for setting up treatment conditions based on treatment area information;

image information input means for inputting image information for diagnosis;

information overlaying means for overlaying the setup treatment area information on the input image information;

information manipulating means for manipulating at least one of the treatment area information or the image information;

an overlapping area warning means which issues a warning when an overlapping area exists in a preset energy irradiation area; and said treatment planning means setting up irradiation areas of energy of the treatment area information by establishing a coordinate of a single reference point.

34. A thermal treatment apparatus for thermally treating by irradiating living bodies with energy comprising:

energy supplying means for supplying energies for treatment;

energy irradiating means for irradiating living bodies with energies supplied;

treatment planning means for setting up at least two treatment areas to be irradiated with energies as treatment area information and for setting up irradiation areas of energy of the treatment area information by establishing a coordinate of a single reference point which can be set up at an arbitrary position within a predetermined area;

selection means for arbitrarily selecting areas to be treated among preset treating areas; and setup means for setting up treatment conditions based on the selected treatment areas.

35. A thermal treatment apparatus for thermally treating by irradiating living bodies with energy comprising:

energy supplying means for supplying energies for treatment;

energy irradiating means for irradiating living bodies with energies supplied;

treatment planning means for setting up at least two treatment areas to be irradiated with energies as treatment area information and for setting up irradiation areas of energy of the treatment area information by establishing a coordinate of a single reference point;

overlapping area warning means which issues a warning when overlapping area exists in a preset energy irradiation area;

selection means for arbitrarily selecting areas to be treated among preset treating areas; and setup means for setting up treatment conditions based on the selected treatment areas.

36. A thermal treatment apparatus for thermally treating by irradiating living bodies with energy comprising:

energy supplying means for supplying energies for treatment;

energy irradiating means for irradiating living bodies with energies supplied;

treatment planning means for setting up at least two treatment areas to be irradiated with energies as treatment area information;

selection means for arbitrarily selecting areas to be treated among preset treating areas;

setup means for setting up treatment conditions based on the selected treatment areas;

recording means for recording the areas where energy irradiations are executed among the treatment areas set up by said treatment planning means; and said selection means preventing already irradiated areas recorded in said recording means from being selected.

* * * * *